United States Patent
Corbett et al.

(10) Patent No.: US 6,448,399 B1
(45) Date of Patent: Sep. 10, 2002

(54) FUSED HETEROAROMATIC GLUCOKINASE ACTIVATORS

(75) Inventors: Wendy Lea Corbett, Randolph; Joseph Samuel Grimsby, Morganville; Nancy-Ellen Haynes, Cranford; Robert Francis Kester; Paige Erin Mahaney, both of West Orange; Ramakanth Sarabu, Pine Brook, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/007,091

(22) Filed: Dec. 4, 2001

Related U.S. Application Data
(60) Provisional application No. 60/251,637, filed on Dec. 6, 2000.

(51) Int. Cl.$^7$ ................. C07D 253/10; C07D 239/70; C07D 239/72; C07D 241/36; C07D 215/46
(52) U.S. Cl. ............... 544/183; 544/283; 544/353; 546/152; 564/155
(58) Field of Search ................. 546/152; 544/183, 544/283, 353; 564/155

(56) References Cited

U.S. PATENT DOCUMENTS
6,320,050 B1 * 11/2001 Bizzarro et al. ............ 544/332

FOREIGN PATENT DOCUMENTS
WO    WO 00/58293    5/2000

OTHER PUBLICATIONS

Colowick, S.P., The Enzymes, vol. 9 (P. Boyer, ed.) Academic Press, New York, New York, pp. 1–48 (1973).
Chipkin et al., Joslin's Diabetes Mellitus (C. R. Kahn and G.C. Wier, eds.) Lea & Febiger, Philiadelphia, PA, pp. 97–115 (1994).
Printz et al., Ann. Rev. Nutrition, vol. 13 (R.E. Olson, D. M. Bier and D.B. McCormick, eds.) Annual Review, Inc., Palo Alto, CA, pp. 463–496 (1993).
Meglasson et al., Amer. J. Physiol., 246, E1–E13 (1984).
Grupe et al., Cell, 83, pp. 69–78 (1995).
Ferre et al., FASEB J., 10, pp. 1213–1218 (1996).
Liang et al., Biochem. J., 309, pp. 167–173 (1995).
Glaser et al., New England J. Med., 338, pp. 226–230 (1998).
Skeean et al., Synthesis, pp. 628–630 (1990).
Boswell et al., J. Org. Chem., 60, pp. 6592–6594 (1995).
Sheikh et al., J. Org. Chem., 47, pp. 4341–4344 (1982).
Brown et al., J. Org. Chem., pp. 4707–4708 (1961).
Wrobel et al., J. Med. Chem., 32, pp. 2493–2500 (1989).
Greenlee et al., J. Org. Chem., 46 pp. 5351–5353 (1981).
Testaferri et al., Synthesis, pp. 751–757 (1983).
Ulman et al., J. Org. Chem., 54, pp. 4691–4692 (1989).
Levine et al., J. Med. Chem., pp. 1029–1032 (1972).
D.J. milner, Synthetic Commun., 22, pp. 73–82 (1992).
Fukuhara et al., J. Fluorine Chem., pp. 299–304 (1991).
Myers et al., J. Am. Chem. Soc., pp. 6496–6511 (1997).
Ahmar et al., Tetradron Lett., pp. 7053–7056 (1989).

* cited by examiner

*Primary Examiner*—Mukund J. Shah
*Assistant Examiner*—Venkataraman Balasubramanian
(74) *Attorney, Agent, or Firm*—George W. Johnston; Dennis P. Tramaloni

(57) ABSTRACT

Glucokinase activating amides are useful for increasing insulin secretion in the treatment of type II diabetes.

17 Claims, No Drawings

FUSED HETEROAROMATIC GLUCOKINASE ACTIVATORS

This application claims benefit of U.S. Provisional application No. 60/251,637, filed on Dec. 6, 2000.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of formulae Ia, Ib, IIa or IIb:

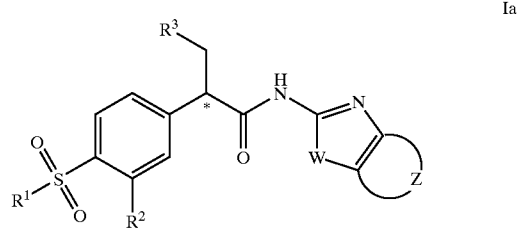

Ia wherein $R^1$ is an alkyl having from 1 to 3 carbon atoms; $R^2$ is hydrogen, halo, nitro, cyano, or perfluoro-methyl; $R^3$ is a cycloalkyl having from 4 to 7 carbon atoms or 2-propyl; Z is —CH₂—CH₂—CH₂—CH₂— or —CH=CR⁴—CH=CH—, wherein $R^4$ is hydrogen, halo, or an alkyl sulfone having from 1 to 3 carbon atoms; W is O, S or NH; and * denotes an asymmetric carbon atom; or a pharmaceutically acceptable salt thereof; or

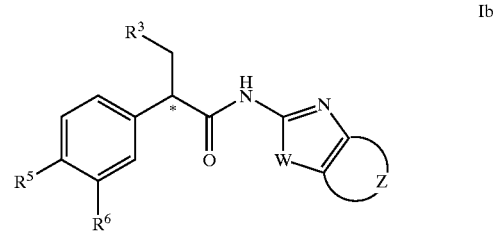

Ib wherein $R^3$ is a cycloalkyl having from 4 to 7 carbon atoms or 2-propyl; $R^5$ is a halogen, preferably Cl or F; $R^6$ is a halogen, preferably Cl or F; Z is —CH₂—CH₂—CH₂—CH₂— or —CH=CR⁴—CH=CH—, wherein $R^4$ is hydrogen, halo, or an alkyl sulfone having from 1 to 3 carbon atoms; W is O, S or NH; and * denotes an asymmetric carbon atom; or a pharmaceutically acceptable salt thereof; or

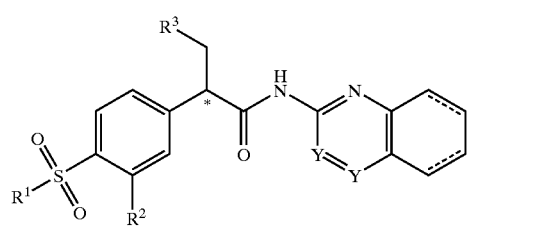

IIa wherein $R^1$ is an alkyl having from 1 to 3 carbon atoms; $R^2$ is hydrogen, halo, nitro, cyano, or perfluoro-methyl; $R^3$ is a cycloalkyl having from 4 to 7 carbon atoms or 2-propyl; each Y is independently CH or N; dotted lines collectively represent 0 or 2 additional double bonds in the heterocyclic ring structure; and * denotes an asymmetric carbon atom; or a pharmaceutically acceptable salt thereof; or

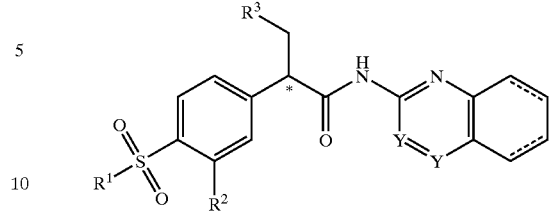

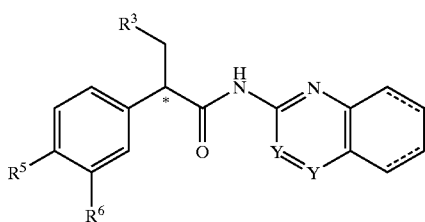

wherein $R^3$ is a cycloalkyl having from 4 to 7 carbon atoms or 2-propyl; $R^5$ is a halogen, preferably Cl or F; $R^6$ is a halogen, preferably Cl or F; each Y is independently CH or N; dotted lines collectively represent 0 or 2 additional double bonds in the heterocyclic ring structure; and * denotes an asymmetric carbon atom; or a pharmaceutically acceptable salt thereof.

The compounds of formulae Ia, Ib, IIa and IIb have been found to activate glucokinase in vitro. Glucokinase activators are useful for increasing insulin secretion in the treatment of type II diabetes.

DETAILED DESCRIPTION OF THE INVENTION

This invention provides a compound, comprising an amide of the formulae Ia, Ib, IIa or IIb:

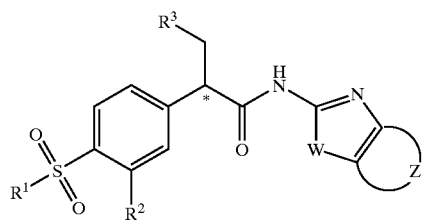

wherein $R^1$ is an alkyl having from 1 to 3 carbon atoms; $R^2$ is hydrogen, halo, nitro, cyano, or perfluoro-methyl; $R^3$ is a cycloalkyl having from 4 to 7 carbon atoms or 2-prpoyl; Z is —CH$_2$—CH$_2$—CH$_2$—CH$_2$—or —CH=CR$^4$—CH=CH—, wherein $R^4$ is hydrogen, halo, or an alkyl sulfone having from 1 to 3 carbon atoms; and W is O, S or NH; or a pharmaceutically acceptable salt thereof; or

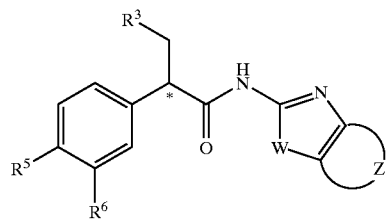

wherein $R^3$ is a cycloalkyl having from 4 to 7 carbon atoms or 2-propyl; $R^5$ is Cl or F; $R^6$ is Cl or F; Z is —CH$_2$—CH$_2$—CH$_2$—CH$_2$—or —CH=CR$^4$—CH=CH—,wherein $R^4$ is hydrogen, halo, or an alkyl sulfone having from 1 to 3 carbon atoms; and W is O, S or NH; or a pharmaceutically acceptable salt thereof; or wherein $R^1$ is an alkyl having from 1 to 3 carbon atoms; $R^2$ is hydrogen, halo, nitro, cyano, or perfluoro-methyl; $R^3$ is a cycloalkyl having from 4 to 7 carbon atoms or 2-propyl; each Y is independently CH or N; dotted lines collectively represent 0 or 2 additional double bonds in the heterocyclic ring structure; or a pharmaceutically acceptable salt thereof, or

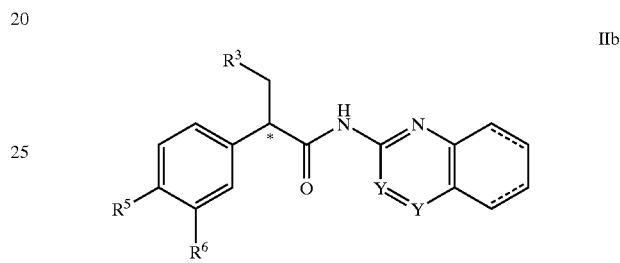

wherein $R^3$ is a cycloalkyl having from 4 to 7 carbon atoms or 2-propyl; $R^5$ is Cl or F; $R^6$ is Cl or F; each Y is independently CH or N; and dotted lines collectively represent 0 or 2 additional double bonds in the heterocyclic ring structure; or a pharmaceutically acceptable salt thereof.

In formulae Ia, Ib, IIa and IIb, * indicates an asymmetric carbon. A compound of formulae Ia, Ib, IIa or IIb may be present either as a racemate or in the "R" configuration at the asymmetric carbon shown. Compounds which are isolated "R" enantiomers are preferred.

In further preferred embodiments of formulae Ia, Ib, IIa and IIb, $R^3$ is a cyclopentyl group.

In formulae IIa and IIb, the dotted lines collectively represent zero or two, preferably two additional double bonds in the heterocyclic ring. As an example, in 3-cyclopentyl-2-(3, 4-dichloro-phenyl)-N-quinolin-2-yl-propionamide, there are two additional double bonds in the heterocyclic ring.

In certain preferred amides of formulae Ia and IIa, $R^1$ is CH$_3$ and $R^2$ is H. Examples of such amides are N-benzothiazol-2-yl-3-cyclopentyl-2-(4-methanesulfonyl-phenyl)-propionamide and 3-cyclopentyl-2-(4-methanesulfonyl-phenyl)-N-quinolin-2-yl-propionamide.

In further preferred amides of formulae Ia and IIa, $R^1$ is SO$_2$CH$_3$ and $R^2$ is halo. Examples of such amides are N-benzooxazol-2-yl-2(R)-(3-chloro-4-methanesulfonyl-phenyl)-3-cyclopentyl-propionamide; 2(R)-(3-chloro-4-methanesulfonyl-phenyl)-3-cyclopentyl-N-quinolin-2-yl-propionamide; N-(1H-benzoimidazol-2-yl)-2-(3-bromo-4-methanesulfonyl-phenyl)-3-cyclopentyl-propionamide; and 2-(3-bromo-4-methanesulfonyl-phenyl)-3-cyclopentyl-N-quinolin-2-yl-propionamide.

In yet further preferred amides of formulae Ia and IIa, $R^1$ is CH$_3$ and $R^2$ is CN. Examples of such amides are N-benzothiazol-2-yl-2-(3-cyano-4methanesulfonyl-phenyl)-3-cyclopentyl-propionamide; N-benzooxazol-2-yl-2-(3-cyano-4-methanesulfonyl-phenyl)-3-cyclopentylpropionamide; N-(1H-benzoimidazol-2-yl)-2-(3-cyano-4-methanesulfonyl-phenyl-)3-cyclopentyl-propionamide; and 2-(3-cyano-4-methanesulfonyl-phenyl)-3-cyclopentyl-N-quinolin-2-yl-propionamide.

In still other preferred amides of formulae Ia and IIa, $R^1$ is $CH_3$ and $R^2$ is $CF_3$. Examples of such amides are 3-cyclopentyl-2-(4-methanesulfonyl-3-trifluoromethyl-phenyl)-N-quinolin-2-yl-propionamide; N-benzothiazol-2-yl-3-cyclopentyl-2-(4-methanesulfonyl-3-trifluoromethyl-phenyl)-propionamide; N-(1H-benzoimidazol-2-yl)-3-cyclopentyl-2-(4-methanesulfonyl-3trifluoromethyl-phenyl)-propionamide; and N-benzooxazol-2-yl-3-cyclopentyl-2-(4-methanesulfonyl-3-trifluoromethyl-phenyl)-propionamide.

In still further amides of formulae Ia and IIa, $R^1$ is $CH_3$, and $R^2$ is $NO_2$. Examples of such amides are N-benzothiazol-2-yl-3-cyclopentyl-2-(4-methanesulfonyl-3-nitro-phenyl)-propionamide; N-benzooxazol-2-yl-3-cyclopentyl-2-(4-methanesulfonyl-3-nitro-phenyl)-propionamide; N-(1H-benzoimidazol-2-yl)-3-cyclopentyl-2-(4-methanesulfonyl-3-nitro-phenyl)-propionamide; and 3-cyclopentyl-2-(4-methanesulfonyl-3-nitro-phenyl)-N-quinolin-2-yl-propionamide.

In certain amides of formulae Ia and Ib, W is O. Examples of such amides include N-benzooxazol-2-yl-3-cyclopentyl-2(R)-(3,4-dichloro-phenyl)-propionamide; and N-benzooxazol-2-yl-3-cyclopentyl-2-(4-methanesulfonyl-phenyl)-propionamide.

In certain other amides of formulae Ia and Ib, W is S. Examples of such amides include N-benzothiazol-2-yl-3-cyclopentyl-2-(3,4-dichloro-phenyl)-propionamide; N-benzothiazol-2-yl-2-(3-bromo-4-methanesulfonyl-phenyl)-3-cyclopentyl-propionamide; and N-benzothiazol-2-yl-2-(3-cyano-4-methanesulfonyl-phenyl)-3-cyclopentyl-propionamide.

In still other amides of formulae Ia and Ib, W is NH. Examples of such amides include N-(1H-benzoimidazol-2-yl)-3-cyclopentyl-2-(3,4-dichloro-phenyl)-propionamide; and N-(1H-benzoimidazol-2-yl)-2-(3-chloro-4-methanesulfonyl-phenyl)-3-cyclopentyl-propionamide.

In yet other amides of formulae Ia and Ib, Z is —CH=CR$^4$—CH=CH— and $R^4$ is halo, methyl sulfone or ethyl sulfone. Examples of such amides include 3-cyclopentyl-2-(3,4-dichloro-phenyl)-N-(6-fluoro-benzothiazol-2-yl)-propionamide; and 3-cyclopentyl-2-(3,4-dichlorophenyl)-N-(6-methanesulfonyl-benzothiazol-2-yl)-propionamide.

In certain preferred amides of formulae Ib and IIb, both $R^5$ and $R^6$ are Cl or both $R^5$ and $R^6$ are F. Most preferably, both $R^5$ and $R^6$ are Cl.

In certain amides of formulae IIa and IIb, both Y are CH. Examples of such amides include 3-cyclopentyl-2-(3,4-dichloro-phenyl)-N-quinolin-2-yl-propionamide; 3-cyclopentyl-2-(4-methanesulfonyl-phenyl)-N-quinolin-2-yl-propionamide; 2(R)-(3-chloro-4-methanesulfonyl-phenyl)-3-cyclopentyl-N-quinolin-2-yl-propionamide; 2-(3-chloro-4-methanesulfonyl-phenyl)-3-cyclopentyl-N-quinolin-2-yl-propionamide; 2-(3-bromo-4-methanesulfonyl-phenyl)-3-cyclopentyl-N-quinolin-2-yl-propionamide; 2-(3-cyano-4-methanesulfonyl-phenyl)-3-cyclopentyl-N-quinolin-2-yl-propionamide; 3-cyclopentyl-2-(4-methanesulfonyl-3-trifluoromethyl-phenyl)-N-quinolin-2-yl-propionamide; and 3-cyclopentyl-2-(4-methanesulfonyl-3-nitro-phenyl)-N-quinolin-2-yl-propionamide.

In certain other amides of formulae IIa and IIb, at least one Y is N.

In still other amides of formulae IIa and IIb, the dotted lines collectively represent two additional double bonds. Examples of such amides include 3-cyclopentyl-2-(3,4-dichloro-phenyl)-N-quinolin-2-yl-propionamide; 3-cyclopentyl-2-(4-methanesulfonyl-phenyl)-N-quinolin-2-yl-propionamide; 2(R)-(3-chloro-4-methanesulfonyl-phenyl)-3-cyclopentyl-N-quinolin-2-yl-propionamide; 2-(3-chloro-4-methanesulfonyl-phenyl)-3-cyclopentyl-N-quinolin-2-yl-propionamide; 2-(3-bromo-4-methanesulfonyl-phenyl)-3-cyclopentyl-N-quinolin-2-yl-propionamide; 2-(3-cyano-4-methanesulfonyl-phenyl)-3-cyclopentyl-N-quinolin-2-yl-propionamide; 3-cyclopentyl-2-(4-methanesulfonyl-3-trifluoromethyl-phenyl)-N-quinolin-2-yl-propionamide; and 3-cyclopentyl-2-(4-methanesulfonyl-3-nitro-phenyl)-N-quinolin-2-yl-propionamide.

In yet other amides of formulae Ia and IIb, the dotted lines collectively represent zero additional double bonds.

As used herein, the term "halogen" and the term "halo", unless otherwise stated, designate all four halogens, i.e. fluorine, chlorine, bromine and iodine. A preferred halogen is chlorine.

As used throughout this application, the term "lower alkyl" includes both straight chain and branched chain alkyl groups having from 1 to 8 carbon atoms, preferably from 1 to 3 carbon atoms, such as methyl, ethyl, propyl, isopropyl, preferably methyl.

As used herein the term "aryl" signifies aryl mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl.

As used herein, the term "lower alkoxy" includes both straight chain and branched chain alkoxy groups having from 1 to 7 carbon atoms, such as methoxy, ethoxy, propoxy, isopropoxy, preferably methoxy and ethoxy.

As used herein, the term "lower alkanoic acid" denotes lower alkanoic acids containing from 2 to 7 carbon atoms such as propionic acid, acetic acid and the like.

The term "aroyl" denotes aroic acids wherein aryl is as defined hereinbefore, with the hydrogen group of the COOH moiety removed. Among the preferred aroyl groups is benzoyl.

As used herein, "lower alkyl thio" means a lower alkyl group as defined above where a thio group is bound to the rest of the molecule.

As used herein, "lower alkyl sulfonyl" means a lower alkyl group as defined above where a sulfonyl group is bound to the rest of the molecule.

As used herein, "cycloalkyl" means a saturated hydrocarbon ring having from 3 to 10 carbon atoms, preferably from 3 to 7 carbon atoms. A preferred cycloalkyl is cyclopentyl.

As used herein, the term "lower alkoxy" includes both straight chain and branched chain alkoxy groups having from 1 to 7 carbon atoms, such as methoxy, ethoxy, propoxy, isopropoxy, preferably methoxy and ethoxy.

During the course of the reaction the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for those purposes are those in which the acyl moieties are derived from a lower alkanoic, aryl lower alkanoic, or lower alkane dicarboxyclic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxcyclic acid anhydrides, e.g. succinic anhydride as well as chloro formates e.g. trichloro and ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2.0 to 3. Particularly preferred amino protecting groups are t-butylcarbamate (BOC), benzylcarbamate (CBZ), and 9-fluorenylmethylcarbamate (FMOC).

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, paratoluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

The compounds of formulae Ia, Ib, IIa and IIb can be prepared starting from the compound of formula V by the following Reaction Scheme:

Reaction Scheme

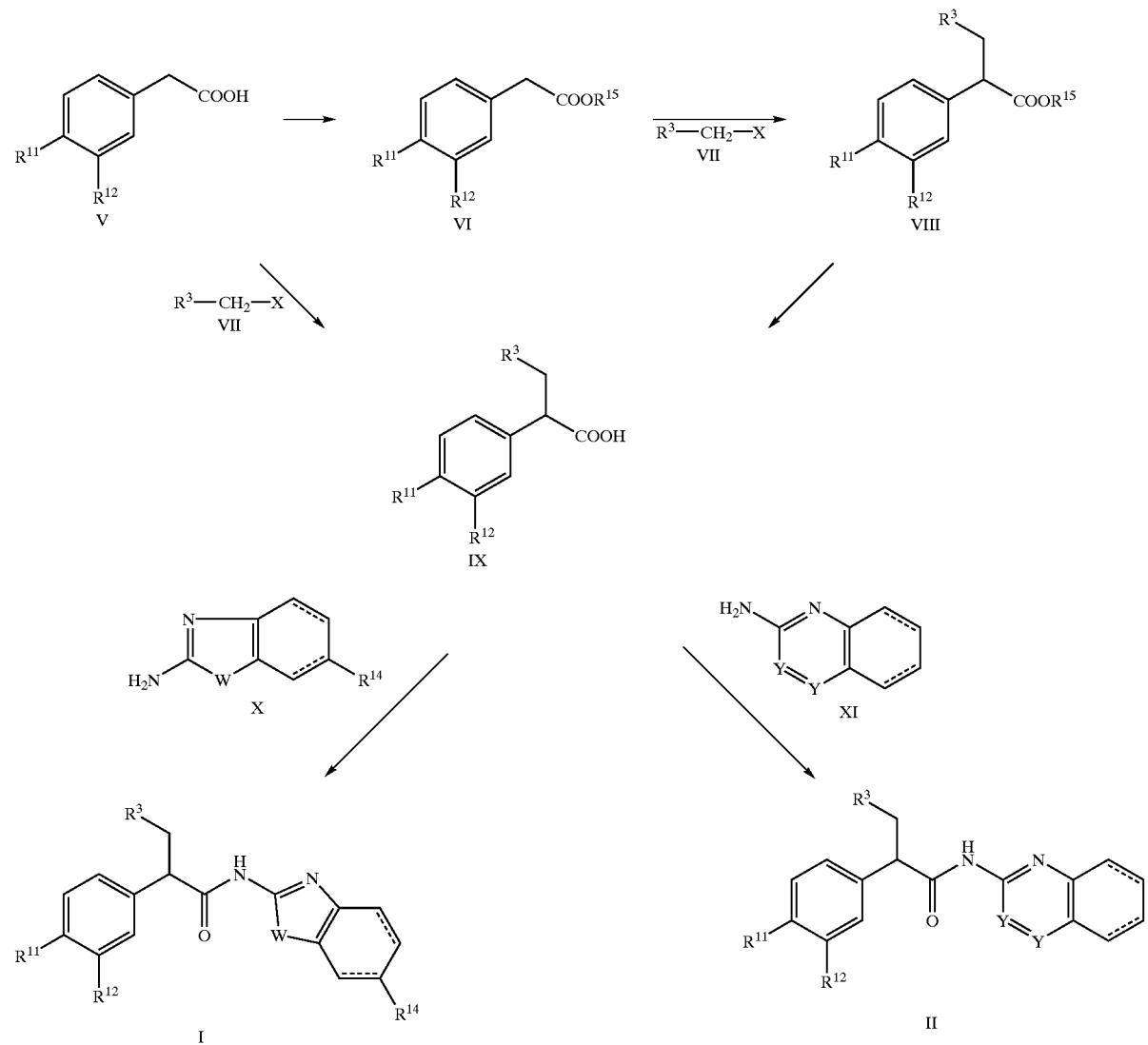

wherein $R^{11}$ is Cl, F or an alkyl sulfone of 1 to 3 carbon atoms, and $R^{12}$ is Cl or F when $R^{11}$ is Cl or F and $R^{12}$ is hydrogen, halo, nitro, cyano, or perfluoro-methyl when $R^{11}$ is an alkyl sulfone; $R^3$, W, and Y are as above, the dotted lines represent 0 or 2 additional double bonds in the heterocyclic ring, $R^{14}$ is hydrogen when the dotted lines represent 0 additional double bonds, and $R^{14}$ is hydrogen, halo, or an alkyl sulfone having from 1 to 3 carbon atoms when the dotted lines represent 2 additional double bonds, $R^{15}$ is a hydrolyzable ester group and X is a halogen atom, preferably Br or I.

The carboxylic acids of formula V are known wherein $R^{12}$ is hydrogen and $R^{11}$ is mercapto (4-mercaptophenylacetic acid), methylthio (4-methylthiophenylacetic acid), or methylsulfonyl (4-methylsulfonylphenylacetic acid). The carboxylic acids of formula V wherein both of $R^{11}$ and $R^{12}$ are chloro or fluoro (3,4-dichlorophenylacetic acid and 3,4-difluorophenyl acetic acid, respectively) are known. The carboxylic acid of formula V wherein $R^{11}$ is fluoro and $R^{12}$ is chloro is also known (3-chloro-4-fluorophenylacetic acid). If necessary for further chemical modification to produce the desired substitutions at $R^{11}$ and $R^{12}$, the carboxylic acids can be converted to the corresponding esters of lower alkyl alcohols using any conventional esterification methods.

All the reactions hereto forward are to be carried out on the lower alkyl esters of the carboxylic acids of formulae VI or VIII or may be carried out on the carboxylic acids of formulae V or IX themselves.

If it is desired to produce the compound of formula V wherein $R^{11}$ is chloro and $R^{12}$ is fluoro, the commercially available 4-chloro-3-fluorobenzoic acid may be used as starting material. In this reaction sequence, the 4-chloro-3-fluorobenzoic acid is first converted to the corresponding acyl chloride. Any conventioanl method of converting a carboxylic acid to an acyl chloride may be utilized to effect this conversion. This acyl chloride is then converted to the corresponding 4-chloro-3-fluorophenylacetic acid via the Arndt-Eistert synthesis of converting an acyl halide to a carboxylic acid with one additional carbon (see for example, Skeean, R. W.; Goel, O. P. *Synthesis* 1990, 628).

If it is desired to produce compounds of formula V where $R^{12}$ is hydrogen and $R^{11}$ is lower alkyl sulfonyl, the known 4-mercaptophenylacetic acid may be used as a starting material. The compound of formula V where $R^{12}$ is hydrogen and $R^{11}$ is mercapto may be alkylated by conventional methods (for example, with an alkyl halide) to the corresponding lower alkyl thio compounds of formula V. The lower alkyl thio compounds can then be converted to the corresponding lower alkyl sulfonyl compounds of formula V by oxidation. Any conventional method of oxidizing an alkyl thio substituent to the corresponding sulfone group can be utilized to effect this conversion.

On the other hand, if it is desired to produce the compounds of formula V where $R^{12}$ is trifluoromethyl and $R^{11}$ is lower alkyl sulfonyl, the known 4-fluoro-3-(trifluoromethyl)phenyl acetic acid can be used as a starting material. In this reaction, any conventional method of nucleophilic displacement of an aromatic fluorine group with a lower alkyl thiol can be utilized to effect this conversion (see for example, Boswell, G. E.; Licause, J. F. *J. Org. Chem.* 1995, 6592; Sheikh, Y. M. et al. *J. Org. Chem.* 1982, 4341; Brown, F. C. et al. *J. Org. Chem.* 1961, 4707). Once the compounds of formula V where $R^{12}$ is trifluoromethyl and $R^{11}$ is lower alkyl thio are available, they can be converted to the corresponding compounds of formula V where $R^{12}$ is trifluoromethyl and $R^{11}$ is lower alkyl sulfonyl using conventional oxidation procedures.

If it is desired to produce the compounds of formula V where $R^{12}$ is bromo and $R^{11}$ is lower alkyl sulfonyl, the compounds wherein $R^{12}$ is hydrogen and $R^{11}$ is lower alkyl thio, compounds produced as described above, can be used as starting materials. The phenyl acetic acid derivatives of formula V wherein $R^{12}$ is hydrogen and $R^{11}$ is lower alkyl thio can be brominated. Any conventional method of aromatic bromination can be utilized to effect this conversion (see for example, Wrobel, J. et al. *J. Med. Chem.* 1989, 2493). Once the compounds of formula V where $R^{12}$ is bromo and $R^{11}$ is lower alkyl thio are available, they can be converted to the corresponding compounds of formula V where $R^{12}$ is bromo and $R^{11}$ is lower alkyl sulfonyl by oxidation. Any conventional method of oxidizing an alkyl thio substituent to the corresponding sulfone group can be utilized to effect this conversion.

On the other hand, if it is desired to produce the compounds of formulae V or VI where $R^{12}$ is nitro and $R^{11}$ is lower alkyl sulfonyl, the known 4-chloro-3-nitrophenyl acetamide can be used as starting material. In this reaction sequence, any conventional method of converting a primary carboxamide to a carboxylic acid or carboxylic ester can be used to effect this conversion (see for example, Greenlee, W. J.; Thorsett, E. D. *J Org. Chem.*, 1981, 5351). These compounds can then be converted to the compounds of formulae V or VI where $R^{12}$ is nitro and $R^{11}$ is lower alkyl thio. Any conventional method of nucleophilic displacement of an aromatic chlorine group with a lower alkyl thiol can be utilized to effect this conversion (see for example, Testaferri, L. et al. *Synthesis* 1983, 751). Once the compounds of formula V or VI where $R^{12}$ is nitro and $R^{11}$ is lower alkyl thio are available, they can be converted to the corresponding compounds of formula V or VI where $R^{12}$ is nitro and $R^{11}$ is lower alkyl sulfonyl by oxidation. Any conventional method of oxidizing an alkyl thio substituent to the corresponding sulfone group can be utilized to effect this conversion. On the other hand, if it is desired to directly produce the compounds of formulae V or VI where $R^{12}$ is nitro and $R^{11}$ is lower alkyl sulfonyl from the compounds of formulae V or VI where $R^{12}$ is nitro and $R^{11}$ is chloro, any conventional method of nucleophilic displacement of an aromatic chlorine group with a lower alkane sulfinate (such as sodium methane sulfinate) can be utilized to effect this conversion (see for example, Ulman, A.; Urankar, E. *J Org. Chem.*, 1989, 4691).

If it is desired to produce compounds of formula V where $R^{12}$ is chloro and $R^{11}$ is lower alkyl sulfonyl, the known 2-chlorothiophenol can be used as starting material. In this reaction sequence, the mercapto group may be alkylated by conventional methods (for example, with a lower alkyl halide) to the corresponding 2-chloro-1-lower alkyl thio benzenes. These compounds can then be converted to the corresponding 3-chloro-4-(lower alkyl thio)-phenyl acetic acids. First, the 2-chloro-1-lower alkyl thio benzenes are acylated with a (lower alkyl)oxalyl chloride (such as methyloxalyl chloride or ethyloxalyl chloride) via a Friedel-Crafts acylation to produce the beta-keto carboxylic ester in the position para to the lower alkyl thio functional group. The beta-keto carboxylic ester is next hydrolyzed by any conventional method to convert a beta-keto carboxylic ester to a beta-keto carboxylic acid. Wolff-Kisner reduction of the resulting beta-keto carboxylic acid will produce the compounds of formula V where $R^{12}$ is chloro and $R^{11}$ is lower alkyl thio (see for example, Levine, S. D. *J. Med. Chem.* 1972, 1029 for a similar reaction sequence). The lower alkyl thio compounds can then be converted to the corresponding lower alkyl sulfonyl compounds of formula V by oxidation.

Any conventional method of oxidizing an alkyl thio substituent to the corresponding sulfone group can be utilized to effect this conversion.

On the other hand, if it is desired to produce the compounds of formula V where $R^{12}$ is cyano and $R^{11}$ is lower alkyl sulfonyl, these compounds can be prepared as described hereinbefore from compounds where $R^{12}$ is bromo and $R^{11}$ is lower alkyl sulfonyl. Any conventional method of nucleophilic displacement of an aromatic bromine group with a cyano group transferring agent [such as copper(I) cyanide] can be utilized to effect this conversion. This conversion can take place either before or after the compound of formula V is converted to the compounds of formulae I and II.

If it is desired to produce the compounds of formula V where $R^{12}$ is fluoro and $R^{11}$ is lower alkyl sulfonyl, these compounds can be prepared as described hereinbefore from compounds where $R^{12}$ is nitro and $R^{11}$ is lower alkyl sulfonyl. The aromatic nitro substituent is first converted to the aromatic amino group. Any conventional method of reducing a nitro group to an amine can be utilized to effect this conversion. The amino group can then be converted to the fluorine group to produce the compounds of formula V where $R^{12}$ is fluoro and $R^{11}$ is lower alkyl sulfonyl. Any conventional method of converting an aromatic amino group to an aromatic fluorine can be utilized to effect this conversion (see for example, Milner, D. J. *Synthetic Commun.* 1992, 73; Fukuhara, T. et al. *J. Fluorine Chem.* 1991, 299). This conversion can take place either before or after the compound of formula V is converted to the compound of formulae I or II.

For the alkylation reaction using the alkyl halide of formula VII, the carboxylic acids of formula V can be directly alkylated or first converted to the corresponding esters of lower alkyl alcohols of formula VI using any conventional esterification methods and then alkylated. In the alkylation step of the Reaction Scheme, the alkyl halide of formula VII is reacted with the compound of formula V to produce the compound of formula IX or reacted with the compound of formula VI to produce the compound of formula VIII. The compounds of formulae V and VI represent an organic acid and an organic acid derivative having an alpha carbon atom, and the compound of formula VII is an alkyl halide so that alkylation occurs at the alpha carbon atom of this carboxylic acid. This reaction is carried out by any conventional means of alkylation of the alpha carbon atom of a carboxylic acid or a lower alkyl ester of a carboxylic acid. Generally, in these alkylation reactions an alkyl halide is reacted with the dianion of the acetic acid or the anion generated from an acetic acid ester. The anion can be generated by using a strong organic base such as lithium diisopropylamide and n-butyl lithium as well as other organic lithium bases. In carrying out this reaction, low boiling ether solvents are utilized such as tetrahydrofuran at low temperatures from −80° C. to about −10° C. being preferred. However any temperature from −80° C. to room temperature can be used.

The compound of formula VIII can be converted to the compound of formula IX by any conventional procedure to convert a carboxylic acid ester to an acid. The compound of formula IX is condensed with the compounds of formulae X or XI via conventional peptide coupling to produce the compounds of formulae I or II, respectively. In carrying out this reaction, any conventional method of condensing a primary amine with a carboxylic acid can be utilized to effect this conversion.

The amine of formula X is a five-membered heteroaromatic ring fused with a aromatic ring which contains six ring members or fused with a saturated six-membered cycloalkyl ring. The five-membered heteroaromatic ring contains 2 heteroatoms selected from the group consisting of oxygen, sulfur, or nitrogen and is connected by a ring carbon to the amine of the amide group shown in formula I. This five-membered heteroaromatic ring contains a first nitrogen heteroatom adjacent to the connecting ring carbon atom, and the other heteroatoms defined by W can be sulfur, oxygen or nitrogen. There are no heteroatoms on the fusion points. Such five-membered heteroaromatic fused rings defined by formula X include, for example, benzothiazole, benzoxazole, benzoimidazole, and tetrahydrobenzothiazole. These heteroaromatic rings are connected via a ring carbon atom to the amide group to form the amides of formula I. The ring carbon atom of the heteroaromatic ring which is connected via the amide linkage to form the compound of formula I cannot contain any substituent.

The amine of formula XI is a six-membered heteroaromatic ring fused with a aromatic ring which contains six ring members or fused with a saturated six-membered cycloalkyl ring. The six-membered heteroaromatic ring contains 1 to 3 nitrogen heteroatoms and is connected by a ring carbon to the amine of the amide group shown in formula II. This six-membered heteroaromatic ring contains a first nitrogen heteroatom adjacent to the connecting ring carbon atom, and if present, Y defines the location of the other nitrogen heteroatoms. There are no heteroatoms on the fusion points. Such six-membered heteroaromatic fused rings defined by formula XI include, for example, quinoline, quinazoline, quinoxaline, benzotriazine, and tetrahydroquinoline. These heteroaromatic rings are connected via a ring carbon atom to the amide group to form the amides of formula II. The ring carbon atom of the heteroaromatic ring which is connected via the amide linkage to form the compound of formula II cannot contain any substituent.

The required amino heteroaromatic compounds of formulae X and XI are commercially available or can be prepared from the reported literature.

The compound of formulae I and II has an asymmetric carbon atom through which the group —$CH_2R^3$ and the acid amide substituents are connected. In accordance with this invention, the preferred stereoconfiguration of this group is R.

If it is desired to produce the R or the S isomer of the compounds of formulae I and II, these compounds can be isolated as the desired isomer by any conventional chemical means. The preferred chemical mean is the use of pseudoephedrine as a chiral auxiliary for the asymmetric alkylation of the phenylacetic acids of formula V (see for example, Myers, A. G. et al. *J Am. Chem. Soc.* 1997, 6496). To form the desired R acids of formula IX, the compounds of formula V where $R^{12}$ is lower alkyl thio and $R^{11}$ is as described above are first converted to the pseudoephedrine amides using 1R,2R-(-)-pseudoephedrine as the desired enantiomer of pseudoephedrine. Any conventional method of converting a carboxylic acid to a carboxamide can be utilized to effect this conversion. The pseudoephedrine amides can undergo highly diastereoselective alkylations with alkyl halides to afford the α-substituted amide products corresponding to formula IX. These highly diastereomerically enriched amides can be converted to the highly enantiomerically enriched R carboxylic acids of formula IX where $R^{12}$ is lower alkyl thio and $R^{11}$ is as described above by conventional acidic hydrolysis methods to convert a carboxamide to a carboxylic acid. These R carboxylic acids of formula IX where $R^{12}$ is lower alkyl thio and $R^{11}$ is as described above can be converted to the R isomers of formulae I and II where $R^{12}$ is lower alkyl thio and $R^{11}$ is as described above. In carrying out this reaction, any conventional method of condensing a primary amine with a carboxylic acid can be utilized to effect this conversion. Once the compounds of formulae I and II where $R^{12}$ is lower alkyl thio and $R^{11}$ is as described above are available, they can be converted to the corresponding R compounds of formulae I and II where $R^{12}$ is lower alkyl sulfonyl and $R^{11}$ is as described above by oxidation. Any conventional method of oxidizing an alkyl thio substituent to the corresponding sulfone group can be utilized to effect this conversion.

On the other hand, the R carboxylic acids of formula IX where $R^{12}$ is lower alkyl thio and $R^{11}$ is as described above can first be oxidized to the R compounds of formula IX where $R^{12}$ is lower alkyl sulfonyl and $R^1$ is as described above. Any conventional method of oxidizing an alkyl thio substituent to the corresponding sulfone group can be utilized to effect this conversion. These compounds can be then converted to the corresponding R compounds of formulae I and II where $R^{12}$ is lower alkyl sulfonyl and $R^{11}$ is as described above. In carrying out this reaction, any conventional method of condensing a primary amine with a carboxylic acid, without racemization, can be utilized to effect this conversion.

Another chemical means to produce the R or S isomer of the compounds of formulae I or II is to react the compound of formula IX with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction. In the resolution step, the compound of formula IX is reacted with the optically active base in an inert organic solvent medium to produce salts of the optically active amine with both the R and S isomers of the compound of formula IX. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula IX in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula IX which is produced by this method of resolution is carried out throughout the entire reaction scheme to produce the desired R or S isomers of formulae I and II.

The resolution of racemates of the compounds of the formula IX can also be achieved via the formation of corresponding diastereomeric esters or amides. These diastereomeric esters or amides can be prepared by coupling the carboxylic acids of the formula IX with a chiral alcohol or a chiral amine. This reaction can be carried out using any conventional method of coupling a carboxylic acid with an alcohol or an amine. The corresponding diastereomers of compounds of the formula IX can then be separated using any conventional separation methods. The resulting pure diastereomeric esters or amides can then be hydrolyzed to yield the corresponding pure R or S isomers. The hydrolysis reaction can be carried out using conventional known methods to hydrolyze an ester or an amide without racemization. Finally, the separation of R and S isomers can also be achieved using an enzymatic ester hydrolysis of any lower alkyl esters corresponding to the compound of the formula IX (see for example, Ahmar, M.; Girard, C.; Bloch, R, *Tetrahedron Lett*, 1989, 7053), which results in the formation of corresponding chiral acid and chiral ester. The ester and the acid can be separated by any conventional method of separating an acid from an ester. The configuration of formula IX which is produced by this method of resolution is carried out throughout the entire reaction scheme to produce the desired R or S isomers of formulae I and II.

All of the compounds of formulae Ia, Ib, IIa and IIb, which include the compounds set forth in the Examples, activate glucokinase in vitro by the procedure of Example A. In this manner, they increase the flux of glucose metabolism which causes increased insulin secretion. Therefore, the compounds of formulae Ia, Ib, IIa and IIb are glucokinase activators useful for increasing insulin secretion.

The following compounds were tested and found to have excellent glucokinase activator in vivo activity when administered orally in accordance with the assay described in Example B:

N-Benzothiazol-2-yl-2(R)-(3-chloro-4-methanesulfonyl-phenyl)-3-cyclopentyl-propionamide N-(1H-benzoimidazol-2-yl)-2-(3-chloro-4-methanesulfonyl-phenyl)-3-cyclopentyl-propionamide 2-(3-chloro-4-methanesulfonyl-phenyl)-3-cyclopentyl-N-quinolin-2-yl-propionamide This invention will be better understood from the following examples, which are for purposes of illustration and are not intended to limit the invention defined in the claims that follow thereafter.

SYNTHESIS EXAMPLES

EXAMPLE 1

3-Cyclopentyl-2-(3,4-dichloro-phenyl)-N-(4,5,6,7-tetrahydro-benzothiazol-2-yl)-propionamide

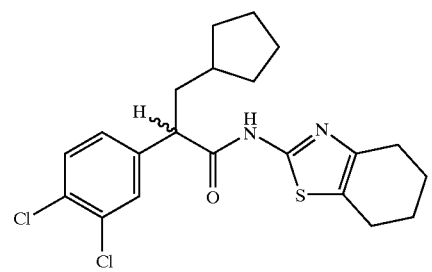

A solution of triphenylphosphine (28.80 g, 109.8 mmol) and imidazole (14.9 g, 219.6 mmol) in methylene chloride (160 mL) was cooled to 0° C. and then slowly treated with iodine (27.87 g, 109.8 mmol). The reaction mixture was then treated dropwise with a solution of cyclopentylmethanol (10.0 g, 99.8 mmol) in methylene chloride (10 mL). The resulting reaction mixture was allowed to warm to 25° C. where it was stirred for 4 h. The reaction mixture was then diluted with water (50 mL), and the reaction mixture was further extracted with methylene chloride (3×20 mL). The combined organic layers were dried over sodium sulfate, filtered, and concentrated in vacuo at 25° C. The resulting solid was washed with pentane (4×50 mL) and filtered through a silica gel plug. The filtrate was concentrated in vacuo at 25° C. to afford iodomethylcyclopentane (18.48 g, 88%) as a clear colorless liquid: EI-HRMS m/e calcd for $C_6H_{11}I$ ($M^+$) 209.9906, found 209.9911.

A solution of diisopropylamine (13.36 mL, 101.89 mmol) in tetrahydrofuran (250 mL) was cooled to −78° C. under a nitrogen atmosphere and then treated with a 2.0M solution of n-butyllithium in hexanes (51 mL, 101.89 mmol). The reaction mixture was stirred at −78° C. for 15 min, at which time, a solution of 3,4-dichlorophenyl acetic acid (9.08 g, 44.3 mmol) in tetrahydrofuran (60 mL) and hexamethylphosphoramide (20 mL) was slowly added via a cannula. The bright yellow solution was allowed to stir at −78° C. for 1 h, at which time, a solution of iodomethylcyclopentane (11.17 g, 53.2 mmol) in hexamethylphosphoramide (10 mL) was added via a cannula. The reaction mixture was stirred at −78° C. for 1 h. The reaction mixture was then allowed to warm to 25° C. where it was stirred for 14 h. The reaction mixture was then acidified to pH=2 by the dropwise addition of a 1N aqueous hydrochloric acid solution and extracted with ethyl acetate (3×50 mL). The combined organic layers were dried over sodium sulfate, filtered, and concentrated in vacuo. Flash chromatography (Merck Silica gel 60, 230–400 mesh, chloroform then 99/1 chloroform/methanol) afforded 3-cyclopentyl-2-(3,4-dichlorophenyl)-propionic acid (10.28 g, 81%) as a white solid: mp 74.5–76.9° C.; EI-HRMS m/e calcd for $C_{14}H_{16}Cl_2O_2$ ($M^+$) 286.0527, found 286.0534.

A solution of 3-cyclopentyl-2-(3,4-dichlorophenyl)-propionic acid (50 mg, 0.17 mmol), benzotriazol-1-yloxy-tris(dimethylamino)phosphonium hexafluorophosphate (83 mg, 0.19 mmol), triethylamine (0.048 mL, 0.34 mmol), and 2-amino-4,5,6,7-tetrahydrobenzothiazole (40 mg, 0.26 mmol) in dry N,N-dimethylformamide (1 mL) was stirred at 25° C. for 14 h. The reaction mixture was then diluted with water and ethyl acetate, and the layers were separated. The organic layer was sequentially washed with a 1N aqueous hydrochloric acid solution, a saturated aqueous sodium chloride solution, and water. The organic layer was dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(3,4-dichloro-phenyl)-N-(4,5,6,7-tetrahydro-benzothiazol-2-yl)-propionamide (56 mg, 79%) as a white solid: mp 170–171° C.; EI-HRMS m/e calcd for $C_{21}H_{24}Cl_2N_2OS$ ($M^+$) 422.0986, found 422.0982.

EXAMPLE 2

N-Benzothiazol-2-yl-3-cyclopentyl-2-(3,4-dichloro-phenyl)-propionamide

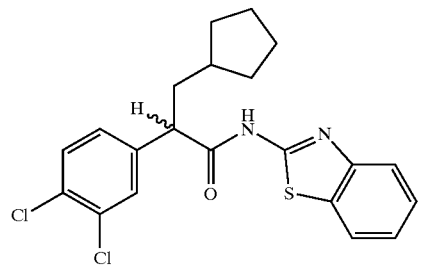

A solution of 3-cyclopentyl-2-(3,4-dichlorophenyl)-propionic acid (prepared as in Example 1, 0.133 g, 0.465 mmol) in methylene chloride (2.5 mL) cooled to 0° C. was treated with a 2M solution of oxalyl chloride in methylene chloride (0.3 mL, 1.0 mmol) and N,N-dimethylformamide (1 drop). The reaction mixture was stirred at 0° C. for 30 min and then treated with a solution of 2-aminobenzothiazole (0.087 g, 0.58 mmol) in methylene chloride (2.5 mL) followed by N,N-diisopropylethylamine (0.2 mL, 2.14 mmol). The reaction mixture was stirred at 25° C. for 16 h. The reaction mixture was then diluted with water (10 mL) and extracted with methylene chloride (3×10 mL). The combined organic layers were sequentially washed with water (1×10 mL), a 1N aqueous sodium hydroxide solution (1×10 mL), a 1N aqueous hydrochloric acid solution (1×10 mL), and a saturated aqueous sodium chloride solution (1×10 mL). The organic layer was dried over sodium sulfate, filtered, and concentrated in vacuo. Flash chromatography (Merck Silica gel 60, 230–400 mesh, 80/20 hexanes/ethyl acetate) afforded the N-benzothiazol-2-yl-3-cyclopentyl-2-(3,4-dichloro-phenyl)-propionamide (0.082 g, 42%) as a white solid: mp 104–105° C.; EI-HRMS m/e calcd for $C_{21}H_{20}Cl_2N_2OS$ ($M^+$) 418.0673, found 418.0674.

EXAMPLE 3

N-Benzothiazol-2-yl-3-cyclopentyl-2(R)-(3,4-dichloro-phenyl)-propionamide

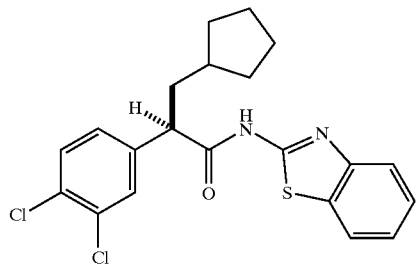

A solution of 3-cyclopentyl-2-(3,4-dichloro-phenyl)-propionic acid (prepared as in Example 1, 5.00 g, 17.4 mmol) in tetrahydrofuran (150 mL) cooled to −78° C. was treated with triethylamine (2.77 mL, 19.9 mmol) followed by trimethylacetyl chloride (2.24 mL, 18.2 mmol). The resulting white slurry was stirred at −78° C. for 15 min and then at 0° C. for 45 min. In a separate flask, a solution of (S)-4-isopropyl-2-oxazolidinone (2.14 g, 16.57 mmol) in tetrahydrofuran (80 mL) cooled to −78° C. was treated with a 2.0M solution of n-butyllithium in hexanes (8.7 mL, 17.4 mmol). The solution was stirred at −78° C. for 10 min and then allowed to warm to 25° C. where it was stirred for an additional 10 min. At this time, the first reaction mixture was then recooled to −78° C. The second reaction mixture was added to the first reaction mixture over a period of 5 min via cannula. The combined reaction was then stirred at −78° C. for 15 min and then allowed to warm to 25° C. where it was stirred for an additional 1.5 h. At this time, the reaction was quenched by the addition of a saturated aqueous sodium bisulfite solution (50 mL) and extracted with ethyl acetate (3×40 mL). The combined organic layers were washed with a saturated aqueous sodium bicarbonate solution (1×20 mL) and a saturated aqueous sodium chloride solution (1×20 mL), dried over sodium sulfate, filtered, and concentrated in vacuo. Flash chromatography (Merck Silica gel 60, 230–400 mesh, 85/15 hexanes/ethyl acetate) afforded two products: (1) 3-[3-cyclopentyl-2(S)-(3,4-dichloro-phenyl)-propionyl]-4(S)-isopropyl-oxazolidin-2-one (2.15 g, 33%) as a clear oil: $[\alpha]^{23}_{589}$=+87.5° (c=0.160, chloroform); EI-HRMS m/e calcd for $C_{20}H_{25}Cl_2NO_3$ ($M^{30}$) 397.1211, found 397.1215; and (2) 3-[3-cyclopentyl-2(R)-(3,4-dichloro-phenyl)-propionyl]-4(S)-isopropyl-oxazolidin-2-one (1.88 g, 28%) as a white solid: mp 71.9–74.6° C.; $[\alpha]^{23}_{589}$=−27.6°(c=0.188, chloroform); EI-HRMS m/e calcd for $C_{20}H_{25}Cl_2NO_3$ ($M^+$) 397.1211, found 397.1212.

A solution of 3-[3-cyclopentyl-2(R)-(3,4-dichloro-phenyl)-propionyl]-4-(S)-isopropyl-oxazolidin-2-one (1.88 g, 4.72 mmol) in tetrahydrofuran (73 mL) and water (22 mL) cooled to 0° C. was treated with a 30% aqueous hydrogen peroxide solution (2.1 mL) and lithium hydroxide (394 mg, 9.4 mmol). The reaction was stirred at 0° C. for 1 h. At this time, the reaction was quenched with a saturated aqueous sodium sulfite solution (16 mL) followed by the addition of a 0.5N aqueous sodium bicarbonate solution (50 mL). The tetrahydrofuran was then removed in vacuo. The residue was diluted with water (40 mL) and extracted with methylene chloride (3×20 mL). The aqueous layer was then acidified to pH=2 with a 5N aqueous hydrochloric acid solution and extracted with ethyl acetate (4×25 mL). The combined organic layers were then dried over sodium sulfate, filtered, and concentrated in vacuo to afford 3-cyclopentyl-2(R)-(3, 4-dichloro-phenyl)-propionic acid (928 mg, 70%) as a white solid: mp 75.1–78.3° C.; $[\alpha]^{23}_{589}$=−50.3° (c=0.100, chloroform); EI-HRMS m/e calcd for $C_{14}H_{16}Cl_2O_2$ (M+) 286.0527, found 286.0535.

A solution of triphenylphosphine (274 mg, 1.04 mmol) in methylene chloride (6 mL) was cooled to 0° C. and then treated with N-bromosuccinimide (211 mg, 1.18 mmol). The resulting brownish-purple mixture was stirred at 0° C. for 5 min until the reaction mixture was homogeneous. The reaction mixture was then treated with 3-cyclopentyl-2(R)-(3,4-dichloro-phenyl)-propionic acid (200 mg, 0.70 mmol). The resulting reaction mixture was stirred at 0° C. for 20 min and then allowed to warm to 25° C. where it was stirred for 30 min. The reaction mixture was then treated with 2-aminobenzothiazole (157 mg, 1.04 mmol) and pyridine (0.17 mL, 2.09 mmol), and the reaction mixture was allowed to stir at 25° C. for 20 h. The resulting reaction mixture was diluted with water (15 mL) and then extracted with methylene chloride (3×15 mL). The combined organic layers were dried over sodium sulfate, filtered, and concentrated in vacuo. Biotage chromatography (FLASH 40S, Silica, 85/15 hexanes/ethyl acetate) afforded N-benzothiazol-2-yl-3-cyclopentyl-2(R)-(3,4-dichloro-phenyl)-propionamide (221 mg, 76%) as a yellow foam: $[\alpha]^{23}_{589}$=−42.4° (c=0.092, chloroform); EI-HRMS m/e calcd for $C_{21}H_{20}Cl_2N_2OS$ (M+) 418.0673, found 418.0672.

EXAMPLE 4

3-Cyclopentyl-2-(3,4-dichloro-phenyl)-N-(6-fluoro-benzothiazol-2-yl)-propionamide

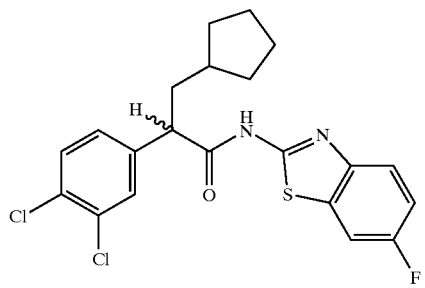

A solution of 3-cyclopentyl-2-(3,4-dichlorophenyl)-propionic acid (prepared as in Example 1, 95.6 mg, 0.33 mmol) in methylene chloride (3.3 mL) cooled to 0° C. was treated with a 2.0M solution of oxalyl chloride in methylene chloride (0.18 mL, 0.36 mmol) and a few drops of N,N-dimethylformamide. The reaction mixture was stirred at 0° C. for 15 min and at 25° C. for 30 min. The reaction mixture was then treated with a solution of 6-fluoro-benzothiazol-2-ylamine (123 mg, 0.73 mmol) in tetrahydrofuran (1.7 mL) and N,N-diisopropylethylamine (0.14 mL, 0.79 mmol). This solution was stirred at 25° C. for 18 h. At this time, the reaction was concentrated in vacuo. Flash chromatography (Merck Silica gel 60, 230–400 mesh, 75/25 hexanes/ethyl acetate) afforded 3-cyclopentyl-2-(3,4-dichloro-phenyl)-N-(6-fluoro-benzothiazol-2-yl)-propionamide (138.4 mg, 95%) as a white solid: mp 131–133° C; FAB-HRMS m/e calcd for $C_2H_{19}FCl_2N_2OS$ (M+H)+437.0657, found 437.0665.

EXAMPLE 5

3-Cyclopentyl-2-(3,4-dichlorophenyl)-N-(6-methanesulfonyl-benzothiazol-2-yl)-propionamide

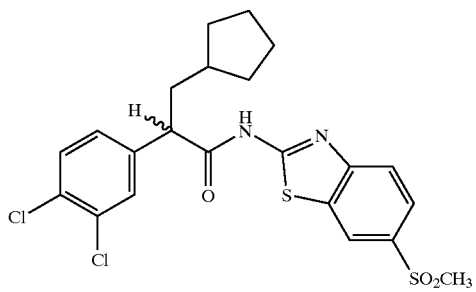

A solution of 3-cyclopentyl-2-(3,4-dichlorophenyl)-propionic acid (prepared as in Example 1, 0.213 g, 0.74 mmol), benzotriazol-1-yloxy-tris(dimethylamino) phosphonium hexafluorophosphate (0.434 g, 0.98 mmol), and 2-amino-6-methanesulfonylbenzothiazole (0.219 g, 0.96 mmol) in methylene chloride (15 mL) at 25° C. was treated with N,N-diisopropylethylamine (0.45 mL, 4.88 mmol). The reaction mixture was stirred at 25° C. for 14 h. The reaction mixture was then diluted with water (10 mL) and extracted with methylene chloride (3×10 mL). The combined organic layers were sequentially washed with water (1×10 mL), a 1N aqueous sodium hydroxide solution (1×10 mL), a 1N aqueous hydrochloric acid solution (1×10 mL), and a saturated aqueous sodium chloride solution (1×10 mL). The organic layer was dried over sodium sulfate, filtered, and concentrated in vacuo. Flash chromatography (Merck Silica gel 60, 230–400 mesh, 80/20 hexanes/ethyl acetate) afforded 3-cyclopentyl-2-(3,4-dichlorophenyl)-N-(6-methanesulfonyl-benzothiazol-2-yl)-propionamide (0.296 g, 80%) as a white solid.

EXAMPLE 6

N-Benzooxazol-2-yl-3-cyclopentyl-2-(3,4-dichlorophenyl)-propionamide

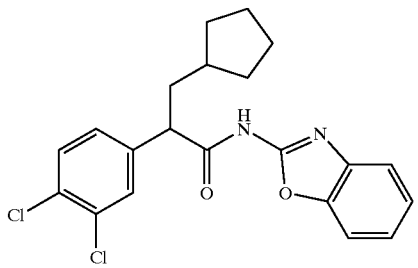

A solution of triphenylphosphine (274 mg, 1.04 mmol) in methylene chloride (6 mL) was cooled to 0° C. and then treated with N-bromosuccinimide (211 mg, 1.18 mmol). The resulting brownish-purple mixture was stirred at 0° C. for 5 min until the reaction mixture became homogeneous. The reaction mixture was then treated with 3-cyclopentyl-2-(3, 4-dichloro-phenyl)-propionic acid (prepared as in Example 1, 200 mg, 0.70 mmol). The reaction mixture was stirred at 0° C. for 20 min and then allowed to warm to 25° C. where it was stirred for 30 min. The reaction mixture was then treated with 2-aminobenzoxazole (140 mg, 1.04 mmol) and pyridine (0.17 mL, 2.09 mmol), and the reaction mixture was allowed to stir at 25° C. for 20 h. The resulting reaction mixture was diluted with water (15 mL) and then extracted with methylene chloride (3×15 mL). The combined organic layers were dried over sodium sulfate, filtered, and concentrated in vacuo. Biotage chromatography (FLASH 40S, Silica, 80/20 hexanes/ethyl acetate) afforded N-benzooxazol-2-yl-3-cyclopentyl-2-(3,4-dichloro-phenyl)-propionamide (214 mg, 76%) as a light yellow foam: EI-HRMS m/e calcd for $C_{21}H_{20}Cl_2N_2O_2$ (M+) 402.0902, found 402.0908.

EXAMPLE 7

N-Benzooxazol-2-yl-3-cyclopentyl-2(R)-(3,4-dichloro-phenyl)-propionamide

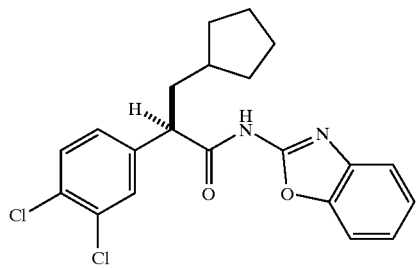

A solution of triphenylphosphine (274 mg, 1.04 mmol) in methylene chloride (6 mL) was cooled to 0° C. and then treated with N-bromosuccinimide (211 mg, 1.18 mmol). The resulting brownish-purple mixture was stirred at 0° C. for 5 min until the reaction mixture became homogeneous. The reaction mixture was then treated with 3-cyclopentyl-2(R)-(3,4-dichloro-phenyl)-propionic acid (prepared as in Example 3, 200 mg, 0.70 mmol). The reaction mixture was stirred at 0° C. for 20 min and then allowed to warm to 25° C. where it was stirred for 30 min. The reaction mixture was then treated with 2-aminobenzoxazole (140 mg, 1.04 mmol) and pyridine (0.17 mL, 2.09 mmol), and the reaction mixture was allowed to stir at 25° C. for 20 h. The resulting reaction mixture was diluted with water (15 mL) and then extracted with methylene chloride (3×15 mL). The combined organic layers were dried over sodium sulfate, filtered, and concentrated in vacuo. Biotage chromatography (FLASH 40S, Silica, 80/20 hexanes/ethyl acetate) afforded N-benzooxazol-2-yl-3-cyclopentyl-2(R)-(3,4-dichloro-phenyl)-propionamide (234 mg, 83%) as a light yellow foam: $[\alpha]^{23}_{589}$=−33.1° (c=0.169, chloroform); EI-HRMS m/e calcd for $C_{21}H_{20}Cl_2N_2O_2$ (M+) 402.0902, found 402.0901.

EXAMPLE 8

N-(1H-Benzoimidazol-2-yl)-3-cyclopentyl-2-(3,4-dichloro-phenyl)-propionamide

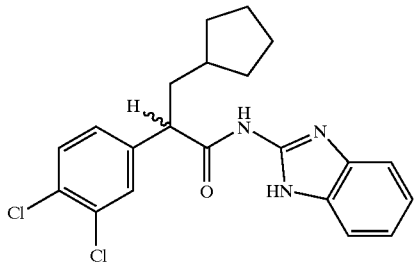

A solution of 3-cyclopentyl-2-(3,4-dichlorophenyl)-propionic acid (prepared as in Example 1, 0.300 g, 1.04 mmol), benzotriazol-1-yloxy-tris(dimethylamino) phosphonium hexafluorophosphate (0.707 g, 1.60 mmol), and 2-aminobenzimidazole (0.213 g, 1.6 mmol) in methylene chloride (10 mL) at 25° C. was treated with triethylamine (0.45 mL, 3.2 mmol). The reaction mixture was stirred at 25° C. for 16 h. The reaction mixture was then diluted with water (20 mL) and extracted with methylene chloride (3×10 mL). The combined organic layers were dried over sodium sulfate, filtered, and concentrated in vacuo. Flash chromatography (Merck Silica gel 60, 230–400 mesh, 80/20 hexanes/ethyl acetate) afforded N-(1H-benzoimidazol-2-yl)-3-cyclopentyl-2-(3,4-dichloro-phenyl)-propionamide (0.396 g, 95%) as a white solid: mp 193.4–196.8° C.; EI-HRMS m/e calcd for $C_{21}H_{21}Cl_2N_3O$ (M+) 401.1062, found 401.1058.

EXAMPLE 9

N-(1H-Benzoimidazol-2-yl)-3-cyclopentyl-2(R)-(3,4-dichloro-phenyl)-propionamide

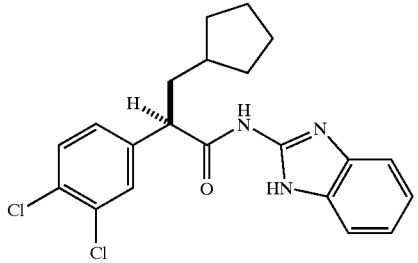

A solution of triphenylphosphine (274 mg, 1.04 mmol) in methylene chloride (6 mL) was cooled to 0° C. and then treated with N-bromosuccinimide (211 mg, 1.18 mmol). The resulting brownish-purple mixture was stirred at 0° C. for 5 min until the reaction mixture became homogeneous. The reaction mixture was then treated with 3-cyclopentyl-2(R)-(3,4-dichloro-phenyl)-propionic acid (prepared as in Example 3, 200 mg, 0.70 mmol). The reaction mixture was stirred at 0° C. for 20 min and then allowed to warm to 25° C. where it was stirred for 30 min. The reaction mixture was then treated with 2-aminobenzimidazole (139 mg, 1.04 mmol) and pyridine (0.17 mL, 2.09 mmol), and the reaction mixture was allowed to stir at 25° C. for 20 h. The resulting reaction mixture was diluted with water (15 mL) and then extracted with methylene chloride (3×15 mL). The combined organic layers were dried over sodium sulfate, filtered, and concentrated in vacuo. Biotage chromatography (FLASH 40S, Silica, 75/25 hexanes/ethyl acetate) afforded N-(1H-benzoimidazol-2-yl)-3-cyclopentyl-2(R)-(3,4-dichloro-phenyl)-propionamide (178 mg, 64%) as an of-white foam: $[\alpha]^{23}_{589}$=−26.7° (c=0.105, chloroform); EI-HRMS m/e calcd for $C_{21}H_{21}Cl_2N_3O$ (M⁺) 401.1062, found 401.1062.

EXAMPLE 10

3-Cyclopentyl-2-(3,4-dichloro-phenyl)-N-quinolin-2-yl-propionamide

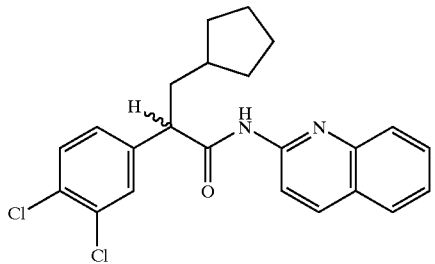

A solution of 3-cyclopentyl-2-(3,4-dichlorophenyl)-propionic acid (prepared as in Example 1, 100 mg, 0.34 mmol), benzotriazol-1-yloxy-tris(dimethylamino)phosphonium hexafluorophosphate (166 mg, 0.38 mmol), triethylamine (0.096 mL, 0.68 mmol), and 2-aminoquinoline (75 mg, 0.52 mmol) in dry N,N-dimethylformamide (2 mL) was stirred at 25° C. for 14 h. The reaction mixture was then diluted with water and ethyl acetate, and the layers were separated. The organic layer was sequentially washed with a saturated aqueous sodium bicarbonate solution, water, and a saturated aqueous sodium chloride solution. The organic layer was dried over magnesium sulfate, filtered, and concentrated in vacuo. Flash chromatography (Merck Silica gel 60, 230–400 mesh, 4/1 hexanes/ethyl acetate) afforded 3-cyclopentyl-2-(3,4-dichloro-phenyl)-N-quinolin-2-yl-propionamide (70 mg, 50%) as a white foam: mp 172–173° C.; EI-HRMS m/e calcd for $C_{23}H_{22}Cl_2N_2O$ (M⁺) 412.1109, found 412.1108.

EXAMPLE 11

3-Cyclopentyl-2(R)-(3,4-dichloro-phenyl)-N-quinolin-2-yl-propionamide

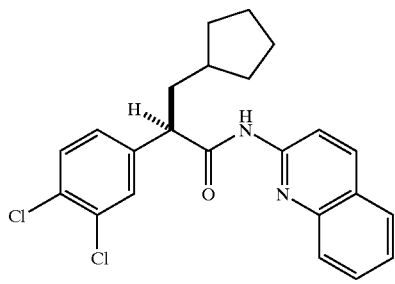

A solution of 3-cyclopentyl-2(R)-(3,4-dichloro-phenyl)-propionic acid (prepared as in Example 3, 100 mg, 0.35 mmol) in methylene chloride (2 mL) was treated with N,N-dimethylformamide (1 drop) and then cooled to 0° C. The reaction mixture was then treated dropwise with a 2M solution of oxalyl chloride in methylene chloride (0.26 mL, 0.52 mmol) and then stirred at 0° C. for 30 min. The resulting reaction mixture was then treated with a solution of 2-aminoquinoline (75 mg, 0.52 mmol) and pyridine (0.14 mL, 1.74 mmol) in tetrahydrofuran (5 mL), and the reaction mixture was allowed to warm to 25° C. The reaction was then stirred at 25° C. for 16 hours. The reaction mixture was diluted with water (10 mL) and extracted with methylene chloride (3×15 mL). The combined organic layers were dried over sodium sulfate, filtered, and concentrated in vacuo. Biotage chromatography (FLASH 40S, Silica, 90/10 hexanes/ethyl acetate) afforded 3-cyclopentyl-2(R)-(3,4-dichloro-phenyl)-N-quinolin-2-yl-propionamide (93 mg, 65%) as an oil: EI-HRMS m/e calcd for $C_{23}H_{22}Cl_2N_2O$ (M⁺) 412.1109, found 412.1123.

EXAMPLE 12

(A) N-Benzothiazol-2-yl-3-cyclopentyl-2-(4-methanesulfonyl-phenyl)-propionamide

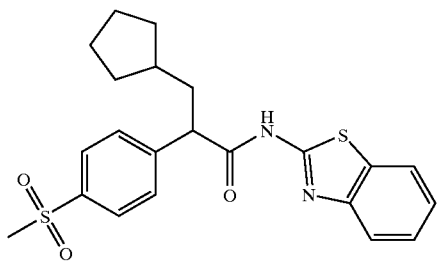

A solution of diisopropylamine (3.2 mL, 23.16 mmol) in dry tetrahydrofuran (10.3 mL) and 1,3-dimethyl-3,4,5,6-tetrahydro-2(1H)-pyrimidinone (3.4 mL) was cooled to −78° C. under nitrogen and then treated with a 10M solution of n-butyllithium in hexanes (2.3 mL, 23.16 mmol). The resulting reaction mixture was stirred at −78° C. for 30 min and then treated dropwise with a solution of 4-(methylthio)phenylacetic acid (2.01 g, 11.03 mmol) in dry tetrahydrofuran (10.3 mL) and 1,3-dimethyl-3,4,5,6-tetrahydro-2(1H)-pyrimidinone (3.4 mL). The reaction mixture was allowed to stir at −78° C. for 1h, at which time, a solution of iodomethylcyclopentane (2.55 g, 12.13 mmol) in a small amount of dry tetrahydrofuran was added dropwise. The reaction mixture was stirred at −78° C. for 30 min and then allowed to warm to 25° C. where it was stirred for 24 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (200 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methylsulfanyl-phenyl)propionic acid (1.01 g, 35%) as a cream solid: mp 91–93° C.; EI-HRMS m/e calcd for $C_{15}H_{20}O_2S$ (M⁺) 264.1184, found 264.1177.

A solution of 3-cyclopentyl-2-(4-methylsulfanyl-phenyl) propionic acid (2.54 g, 9.60 mmol) in formic acid (7 mL) was cooled to 0° C. and then treated with a 30% aqueous hydrogen peroxide solution (8.3 mL, 20.0 mmol). The resulting solution was allowed to warm to 25° C. where it was stirred for 1 h. The reaction was then re-cooled to 0° C., and the product was precipitated by the addition of water (30 mL). The solid was filtered off and dried to afford pure 3-cyclopentyl-2-(4-methanesulfonylphenyl)propionic acid (2.48 g, 87%) as a white solid which was used without further purification: mp 154–159° C.; EI-HRMS m/e calcd for $C_{15}H_{20}O_4S$ (M$^+$) 296.1082, found 296.1080.

A solution of 3-cyclopentyl-2-(4-methanesulfonyl-phenyl)-propionic acid (50 mg, 0.17 mmol), benzotriazol-1-yloxy-tris(dimethylamino)phosphonium hexafluorophosphate (119 mg, 0.27 mmol), triethylamine (70 μL, 0.51 mmol), and 2-aminobenzthiazole (41 mg, 0.27 mmol) in methylene chloride (5 mL) was stirred at 25° C. under nitrogen for 2.33 h. The reaction mixture was partitioned between water and methylene chloride. The organic layer was sequentially washed with a 1N aqueous hydrochloric acid solution (1×10 mL), water (1×10 mL), and a saturated aqueous sodium chloride solution (1×10 mL). The organic layer was dried over magnesium sulfate, filtered, and concentrated in vacuo. Biotage chromatography (FLASH 40S, Silica, 1/1 hexanes/ethyl acetate) afforded N-benzothiazol-2-yl-3-cyclopentyl-2-(4-methanesulfonyl-phenyl)-propionamide (48 mg, 66%) as a white solid: mp 206–209° C.; EI-HRMS m/e calcd for $C_{22}H_{24}N_2O_3S_2$ (M$^+$) 428.1228, found 428.1233.

(B) In An analogous Manner, There Were Obtained

From 3-cyclopentyl-2-(4-methanesulfonyl-phenyl)-propionic acid and 2-aminobenzimidazole: N-(1H-Benzoimidazol-2-yl)-3-cyclopentyl-2-(4-methanesulfonyl-phenyl)-propionamide as a white solid: mp 144–147° C.; EI-HRMS m/e calcd for $C_{22}H_{25}N_3O_3S$ (M$^+$) 411.1615, found 411.1617.

From 3-cyclopentyl-2-(4-methanesulfonyl-phenyl)-propionic acid and 2-aminobenzoxazole: N-Benzooxazol-2-yl-3-cyclopentyl-2-(4-methanesulfonyl-phenyl)-propionamide as a white solid: mp 216–220° C.; EI-HRMS m/e calcd for $C_{22}H_{24}N_2O_4S$ (M$^+$) 412.1458, found 412.1456.

EXAMPLE 13

N-(1H-Benzoimidazol-2-yl)-3-cyclopentyl-2(R)-(4-methanesulfonyl-phenyl)-propionamide

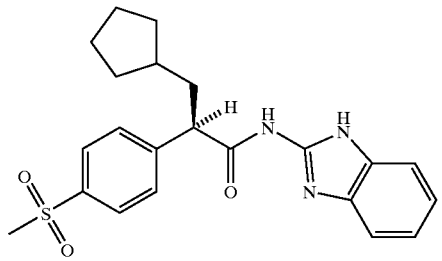

A mixture of 4-(methylthio)phenylacetic acid (50 g, 272 mmol) in tetrahydrofuran (250 mL) was treated with freshly powdered potassium carbonate (93.8 g, 679 mmol). A very mild exotherm ensued, and the resulting white suspension was stirred at 25–26° C. for 30 min. The reaction mixture was then cooled to −10° C. and subsequently treated with trimethylacetyl chloride (35.5 mL, 285 mmol) over 30 min. After completion of the addition, the reaction mixture was stirred at −10° C. to −5° C. for 30 min and then treated with 1R,2R-(−)-pseudoephedrine (59.5 g, 353 mmol) in portions over 15 min while maintaining the temperature of the reaction mixture between −10° C. and −4° C. The reaction mixture was then stirred at −7° C. to 0° C. for 3 h. The reaction mixture was then quenched at 0° C. by the addition of water (150 mL). After vigorously stirring for 10 min, toluene (150 mL) was added, and the reaction mixture was stirred for 5 min. The organic layer was separated and washed with water (2×100 mL). The combined aqueous layers were back-extracted with toluene (1×50 mL). The combined organic layers were washed with a 1N aqueous sulfuric acid solution (1×200 mL), a saturated aqueous sodium bicarbonate solution (1×200 mL), and a solution of water/saturated aqueous sodium chloride solution (1:1, 1×50 mL). The resulting organic layer was then concentrated in vacuo to afford a white solid. This white solid was dried overnight under high vacuum (0.4 mm Hg) to afford crude N-[2(R)-hydroxy-1(R)-methyl-2(R)-phenyl-ethyl]-N-methyl-2-(4-methylsulfanyl-phenyl)-acetamide (82.8 g, 92.6% pure by HPLC analysis). This material was dissolved in toluene (225 mL) at reflux. After standing in a refrigerator over the weekend, the resulting crystalline material was collected by filtration, washed with cold toluene (3×35 mL), and dried under high vacuum to afford the N-[2(R)-hydroxy-1(R)-methyl-2(R)-phenyl-ethyl]-N-methyl-2-(4-methylsulfanyl-phenyl)-acetamide (66.1 g, 73.1%) as white crystals: mp 112–113° C.; 99.6% pure by HPLC analysis. HPLC conditions as follows:

| | |
|---|---|
| Column: | ES Si, 3μ, 5 × 150 mm |
| Mobile Phase: | 30% THF in heptane at 1 mL/min |
| Detection: | UV, 259 nm |
| Retention Time: | 20 min |

A solution of 1,1,1,3,3,3-hexamethyldisilazane (98.4 mL, 457 mmol) in tetrahydrofuran (400 mL) was cooled to −20° C. and then treated with a 2.29M solution of n-butyllithium in hexanes (182 mL, 418 mmol) over 35 min while maintaining the temperature between −20° C. and −15° C. The reaction mixture was stirred at −20° C. for 30 min and then was treated with a solution of N-[2(R)-hydroxy-1(R)-methyl-2(R)-phenyl-ethyl]-N-methyl-2-(4-methylsulfanyl-phenyl)-acetamide (66.1 g, 201 mmol) in tetrahydrofuran (500 mL) over 50 min while maintaining the temperature between −20° C. and −15° C. The resulting yellow solution was stirred at 0° C. for 30 min and then treated with a premixed solution of 1,3-dimethyl-3,4,5,6-tetrahydro-2(1H)-pyrimidinone (51 mL, 418 mmol) and iodomethylcyclopentane (50.6 g, 239 mmol) over 30 min. The resulting reaction mixture was stirred at 0° C. for 4 h, at which time, thin layer chromatography analysis indicated that the reaction was complete. The reaction mixture was then poured into toluene (400 mL). The organic phase was washed sequentially with a solution of water/saturated aqueous sodium chloride solution (1:1, 1×1000 mL), a solution of water/saturated aqueous sodium chloride solution (1:2, 1×1000 mL), a 1M aqueous sulfuric acid solution (1×800 mL), water (1×200 mL), and a saturated aqueous sodium bicarbonate solution (1×1000 mL). The resulting organic layer was concentrated in vacuo to dryness (bath temperature: 35° C. to 40° C.) to afford crude 3-cyclopentyl-N-[2(R)-hydroxy-1(R)-methyl-2(R)-phenyl-ethyl]-N-methyl-2(R)-(4-methylsulfanyl-phenyl)-propionamide as an oily yellow residue (98.5% de by HPLC analysis). This material was dissolved in ethyl acetate (70 mL) and subsequently treated with hexanes (200 mL). The solution was stored in a freezer over the weekend. The resulting solid was collected by filtration, washed with cold hexanes (ca. −10° C., 3×30 mL), and then dried under high vacuum to afford the 3-cyclopentyl-N-[2(R)-hydroxy-1(R)-methyl-2(R)-phenyl-ethyl]-N-methyl-2(R)-(4-methylsulfanyl-phenyl)- propionamide (48.8 g, 59%) as a white solid: mp 82–84° C.; 100% de by HPLC analysis. The combined filtrate and washes were concentrated in vacuo, and the residue (34.4 g) was placed on top of a plug of thin layer chromatography grade silica gel (2–25μ, 70 g). The silica gel plug was then washed with a solution of hexanes/ethyl acetate (4:1, 1.5 L), and the combined eluates were concentrated in vacuo. The resulting pale-yellow oil was dissolved in ethyl acetate (35 mL) and subsequently treated with hexanes (100 mL). The solution was stored in a refrigerator overnight. The resulting solid was collected by filtration, washed with cold hexanes (ca. −10° C., 3×25 mL), and dried under high vacuum to afford an additional batch of 3-cyclopentyl-N-[2(R)-hydroxy-1 (R)-methyl-2(R)-phenyl-ethyl]-N-methyl-2(R)-(4-methylsulfanyl-phenyl)-propionamide (17.3 g, 20.9%) as a white solid: mp 83–85° C.; 99.6% de by HPLC analysis. These two crops were combined to afford the desired diastereomer, 3-cyclopentyl-N-[2(R)-hydroxy-1(R)-methyl-2(R)-phenyl-ethyl]-N-methyl-2(R)-(4-methylsulfanyl-phenyl)-propionamide (66.1 g, 79.9%), as a white solid. HPLC conditions as follows:

| Column: | ES Si, 3μ, 5 × 150 mm |
|---|---|
| Mobile Phase: | 20% THF in heptane at 1 mL/min |
| Detection: | UV, 259 nm |
| Retention Time: | 9.2 min (undesired diastereomer) and 14.4 min (desired diastereomer) |

A solution of 3-cyclopentyl-N-[2(R)-hydroxy-1(R)-methyl-2(R)-phenyl-ethyl]-N-methyl-2(R)-(4-methylsulfanyl-phenyl)-propionamide (4.00 g, 9.72 mmol) in dioxane (8 mL) was treated with a 9N aqueous sulfuric acid solution (7.7 mL). The two-phase mixture was heated at reflux (108° C. bath temperature), resulting in a homogeneous colorless solution. After heating at reflux for 16 h, the reaction mixture was cooled to 5° C. with an ice-water bath and then treated dropwise with water (20 mL) to precipitate the product. After the resulting suspension was stirred for 1 h with ice-water cooling, the solid was collected by filtration, washed with water (4×10 mL), and dried by suction to afford crude 3-cyclopentyl-2(R)-(4-methylsulfanyl-phenyl)-propionic (2.57 g, 96.6%, 96.3% ee by chiral HPLC analysis) as a light tan solid. This material was dissolved in glacial acetic acid (5 mL) at reflux and then treated with water (1 mL) to initiate crystallization. The heating bath was removed, and then water (4 mL) was added dropwise to the suspension to complete the crystallization. The mixture was allowed to cool to ambient temperature. After stirring for 1 h, the solid was collected by filtration. The solid was washed with a solution of acetic acid/water (1:1, 10 mL) and water (4×10 mL), and then dried to afford 3-cyclopentyl-2(R)-(4-methylsulfanyl-phenyl)-propionic (2.24 g, 87.2%) as a white solid: mp 75–76° C.; 96.4% ee by chiral HPLC analysis. Chiral HPLC conditions as follows:

| Column: | Chiralpak AS, 5μ, 5 × 250 mm |
|---|---|
| Mobile Phase: | 6% isopropanol in hexane + 0.1% TFA at 0.5 mL/min |
| Detection: | UV, 259 nm |
| Retention Time: | 13.2 min (desired R-isomer) and 17.1 min (S-isomer) |

A solution of 3-cyclopentyl-2(R)-(4-methylsulfanyl-phenyl)-propionic acid (529 mg, 2.0 mmol) and triphenylphosphine (892 mg, 3.4 mmol) in methylene chloride (10 mL) was cooled to 0° C. and then treated with N-bromosuccinimide (605 mg, 3.4 mmol) in small portions. The reaction mixture color changed from light yellow to a darker yellow then to brown. After the complete addition of N-bromosuccinimide, the reaction mixture was allowed to warm to 25° C. over 30 min. The brown reaction mixture was then treated with 2-aminobenzimidazole (666 mg, 5.0 mmol). The resulting reaction mixture was stirred at 25° C. for 19 h. The reaction mixture was then concentrated in vacuo to remove methylene chloride. The remaining black residue was diluted with a 10% aqueous hydrochloric acid solution (40 mL) and then extracted with ethyl acetate (3×25 mL). The combined organic layers were washed with a saturated aqueous sodium chloride solution (1×20 mL), dried over sodium sulfate, filtered, and concentrated in vacuo. Biotage chromatography (FLASH 40M, Silica, 3/2 hexanes/ethyl acetate then 19/1 ethyl acetate/methanol) afforded N-(1H-benzoimidazol-2-yl)-3-cyclopentyl-2(R)-(4-methanesulfanyl-phenyl)-propionamide (723 mg, 95%) as an off-white solid: mp 180–182° C.; EI-HRMS m/e calcd for $C_{22}H_{25}N_3OS$ (M$^+$) 379.1718, found 379.1715.

A solution of N-(1H-benzoimidazol-2-yl)-3-cyclopentyl-2-(R)-(4-methanesulfanyl-phenyl)-propionamide (152 mg, 0.40 mmol) in formic acid (0.48 mL) and tetrahydrofuran (1 mL) was cooled to 0° C. and then treated with a 30% aqueous hydrogen peroxide solution (0.22 mL, 2.0 mmol). The resulting solution was allowed to warm to 25° C. where it was stirred for 19 h. The reaction was then concentrated in vacuo and was purified via Biotage chromatography (FLASH 40S, Silica, 2% methanol/chloroform) to afford N-(1H-benzoimidazol-2-yl)-3-cyclopentyl-2-(R)-(4-methanesulfonyl-phenyl)-propionamide (103 mg, 63%) as a yellow solid: mp 230–232° C.; $[\alpha]^{23}_{589}$=−84.8° (c=0.033, chloroform); EI-HRMS m/e calcd for $C_{22}H_{25}N_3O_3S$ (M$^+$) 411.1617, found 411.1632.

EXAMPLE 14

N-Benzothiazol-2-yl-3-cyclopentyl-2(R)-(4-methanesulfonyl-phenyl)-propionamide

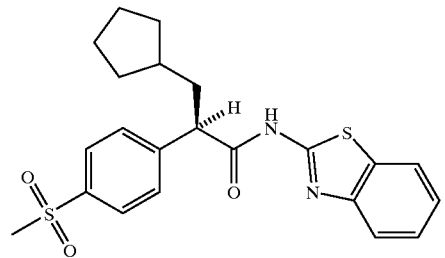

A solution of 3-cyclopentyl-2(R)-(4-methylsulfanyl-phenyl)-propionic acid (prepared as in Example 13, 529 mg, 2.0 mmol) and triphenylphosphine (892 mg, 3.4 mmol) in methylene chloride (10 mL) was cooled to 0° C. and then treated with N-bromosuccinimide (605 mg, 3.4 mmol) in small portions. The reaction mixture color changed from light yellow to a darker yellow then to brown. After the complete addition of N-bromosuccinimide, the reaction mixture was allowed to warm to 25° C. over 30 min. The brown reaction mixture was then treated with 2-aminobenzothiazole (751 mg, 5.0 mmol). The resulting reaction mixture was stirred at 25° C. for 19 h. The reaction mixture was then concentrated in vacuo to remove methylene chloride. The remaining black residue was diluted with a 10% aqueous hydrochloric acid solution (40 mL) and then extracted with ethyl acetate (3×25 mL). The combined organic layers were washed with a saturated aqueous sodium chloride solution (1×20 mL), dried over sodium sulfate, filtered, and concentrated in vacuo. Biotage chromatography (FLASH 40M, Silica, 4/1 hexanes/ethyl acetate) afforded N-benzothiazol-2-yl-3-cyclopentyl-2(R)-(4-methanesulfanyl-phenyl)-propionamide (392 mg, 49%) as white foam; EI-HRMS m/e calcd for $C_{22}H_{24}N_2OS$ (M$^+$) 396.1330, found 396.1328.

A solution of N-(1H-benzoimidazol-2-yl)-3-cyclopentyl-2(R)-(4-methanesulfanyl-phenyl)-propionamide (157 mg, 0.40 mmol) in formic acid (0.48 mL) and tetrahydrofuran (1 mL) was cooled to 0° C. and then treated with a 30% aqueous hydrogen peroxide solution (0.22 mL, 2.0 mmol). The resulting solution was allowed to warm to 25° C. where it was stirred for 19 h. The reaction was then concentrated in vacuo and was purified via Biotage chromatography (FLASH 40S, Silica, 3/2 hexanes/ethyl acetate) to afford the N-benzothiazol-2-yl-3-cyclopentyl-2(R)-(4-methanesulfonyl-phenyl)-propionamide (48 mg, 28%) as a white foam: mp 100–105° C.; $[\alpha]^{23}_{589}$=−48.6° (c=0.035, chloroform); EI-HRMS m/e calcd for $C_{22}H_{24}N_2O_3S$ (M$^+$) 428.1224, found 428.1228.

EXAMPLE 15

3-Cyclopentyl-2-(4-methanesulfonyl-phenyl)-N-quinolin-2-yl-propionamide

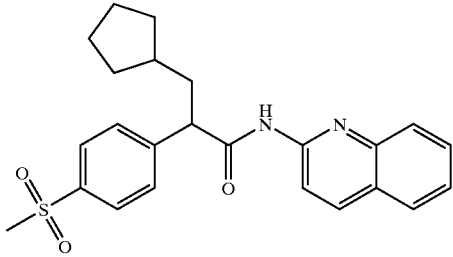

A solution of 3-cyclopentyl-2-(4-methanesulfonyl-phenyl)-propionic acid (prepared as in Example 12, 200 mg, 0.68 mmol) in methylene chloride (8 mL) was treated with dry N,N-dimethylformamide (1 drop). The reaction mixture was cooled to 0° C. and then treated dropwise with a 2M solution of oxalyl chloride in methylene chloride (0.38 mL, 0.78 mmol). The reaction mixture was stirred at 0° C. for 10 min and then stirred at 25° C. for 30 min. The reaction mixture was then treated with N, N-diisopropylethylamine (0.28 mL, 1.64 mmol) followed by a solution of 2-aminoquinoline (208 mg, 1.44 mmol) in dry tetrahydrofuran (1 mL). The resulting reaction mixture was stirred at 25° C. for 17 h. The reaction mixture was concentrated in vacuo. The resulting residue was adsorbed onto silica gel (Merck Silica gel 60, 230–400 mesh) and then purified via Biotage chromatography (FLASH 40S, Silica, 3/2 hexanes/ ethyl acetate) to afford 3-cyclopentyl-2-(4-methanesulfonyl-phenyl)-N-quinolin-2-yl-propionamide (195 mg, 68%) as a white foam; EI-HRMS m/e calcd for $C_{24}H_{26}N_2O_3S$ (M$^+$) 422.1665, found 422.1664.

EXAMPLE 16

N-Benzooxazol-2-yl-2-(3-chloro-4-methanesulfonyl-phenyl)-3-cyclopentyl-propionamide

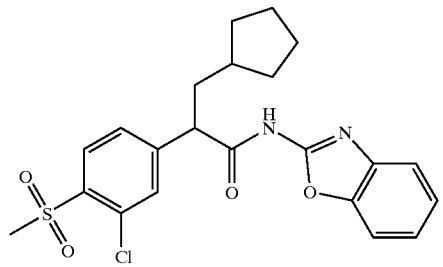

A solution of aluminum trichloride (54.9 g, 412 mmol) in chloroform (180 mL) under argon was cooled to 0° C. and then treated dropwise with a solution of methyl chlorooxoacetate (24.3 mL, 264 mmol) in chloroform (180 mL). The reaction mixture was stirred at 0° C. for 30 min and then was treated dropwise with a solution of 2-chlorothioanisole (39.4 g, 247 mmol) in chloroform (180 mL). The reaction mixture turned red in color. The resulting reaction mixture was allowed to warm to 25° C. where it was stirred for 4 h. The reaction mixture was then slowly poured onto ice (700 mL). The resulting yellow mixture was stirred for 15 min and then was filtered through celite to remove the aluminum salts. The filtrate was then extracted with methylene chloride (3×50 mL). The combined organic layers were washed with a saturated aqueous sodium bicarbonate solution (1×50 mL). The organic layer was then dried over magnesium sulfate, filtered, and concentrated in vacuo to afford (3-chloro-4-methylsulfanyl-phenyl)-oxo-acetic acid methyl ester (36.4 g, 60%) as a light yellow oil: EI-HRMS m/e calcd for $C_{10}H_9ClSO_3$ (M$^+$) 243.9961, found 243.9958.

A solution of (3-chloro-4-methylsulfanyl-phenyl)-oxo-acetic acid methyl ester (61.7 g, 252 mmol) in toluene (120 mL) was heated at 50° C. This heated solution was then treated dropwise with a 3M aqueous sodium hydroxide solution (105 mL, 313 mmol) via a dropping funnel, taking care to keep the temperature below 60° C. After the addition was complete, the reaction mixture was stirred at 50° C. for another 1.5 h, during which time, a yellow precipitate began to form. After this time, the heat was removed, and the warm solution was treated dropwise with concentrated hydrochloric acid (10.6 mL, 290 mmol). The resulting reaction mixture was allowed to cool to 25° C. and then was stirred at 25° C. for 16 h. The solid was filtered and then washed with water (50 mL) and toluene (50 mL). The solid was dried by suction for 1 h and then dried in a high vacuum desiccator to afford (3-chloro-4-methylsulfanyl-phenyl)-oxo-acetic acid (57.22 g, 98%) as a white solid: mp 166° C. (dec); FAB-HRMS m/e calcd for $C_9H_7ClSO_3$ (M+Na)$^+$ 252.9702, found 252.9700.

A reaction flask equipped with mechanical stirrer was charged with hydrazine hydrate (8.5 mL, 273 mmol). The hydrazine hydrate was cooled to −50° C. and then treated with (3-chloro-4-methylsulfanyl-phenyl)-oxo-acetic acid (12.6 g, 54.6 mmol) in one portion. An exotherm ensued that raised the temperature. The resulting white milky mixture was then heated to 80° C. After reaching 80° C., the heating element was removed, and the reaction mixture was then treated with potassium hydroxide (2.09 g, 31.7 mmol) in one portion. An exotherm was observed. The reaction was then stirred at 25° C. until the reaction temperature cooled back to 80° C. At this time, another portion of potassium hydroxide (2.09 g, 31.7 mmol) was added. Again, an exotherm was observed, and the resulting reaction mixture was allowed to cool back to 80° C. Once at 80° C., a third portion of potassium hydroxide (2.09 g, 31.7 mmol) was added to the reaction mixture. Another exotherm was observed, and after cooling back to 80° C., the fourth and final portion of potassium hydroxide (2.09 g, 31.7 mmol) was added. At this point, the heating element was added, and the reaction mixture was heated at 100° C. for 16 h. The resulting homogenous reaction mixture was cooled to 25° C. and then diluted with water (12 mL). The reaction mixture was then transferred to a separatory funnel, rinsing with additional water (12 mL) and diethyl ether (40 mL). The layers were separated, and the aqueous layer was transferred to a flask. The organic layer was extracted with water (2×15 mL) The aqueous layers were combined and treated with heptane (20 mL), and the resulting reaction mixture was vigorously stirred. This stirred solution was then treated dropwise with concentrated hydrochloric acid (26 mL) over 30 min while the temperature was kept under 50° C. with an ice bath. A cloudy suspension formed, and this suspension was stirred at 25° C. for 3 h. The solid that formed was collected by filtration and then washed sequentially with a 1N aqueous hydrochloric acid solution (2×6 mL), heptane (1×12 mL), and a solution of heptane/diethyl ether (15 mL, 4:1). The resulting solid was dried under high vacuum to afford (3-chloro-4-methylsulfanyl-phenyl)-acetic acid (10.48 g, 89%) as an off-white solid: mp 105.6–108.4° C.; EI-HRMS m/e calcd for $C_9H_9ClSO_2$ ($M^+$) 216.0012, found 216.0022.

A solution of (3-chloro-4-methylsulfanyl-phenyl)-acetic acid (8.00 g, 36.92 mmol) in methanol (200 mL) was treated slowly with concentrated sulfuric acid (1 mL). The resulting reaction mixture was heated under reflux overnight. The reaction mixture was allowed to cool to 25° C. and then concentrated in vacuo to remove methanol. The resulting residue was dissolved with ethyl acetate (50 mL). The organic layer was washed with water (1×50 mL). The water layer was further extracted with ethyl acetate (3×20 mL). The combined organic layers were washed with a saturated aqueous sodium bicarbonate solution (1×25 mL). The organic layer was then dried over sodium sulfate, filtered, and concentrated in vacuo to afford (3-chloro-4-methylsulfanyl-phenyl)-acetic acid methyl ester (7.28 g, 85.5%) as a yellow oil which was used without further purification: EI-HRMS m/e calcd for $C_{10}H_{11}ClO_2S$ ($M^+$) 230.0168, found 230.0166.

A solution of diisopropylamine (4.86 mL, 34.70 mmol) in dry tetrahydrofuran (212.3 mL) was cooled to −78° C. and then treated with a 2.5M solution of n-butyllithium in hexanes (13.88 mL, 34.70 mmol). The resulting reaction mixture was stirred at −78° C. for 15 min and then slowly treated with a solution of (3-chloro-1-methylsulfanyl-phenyl)-acetic acid methyl ester (7.28 g, 31.55 mmol) in dry tetrahydrofuran (23.6 mL) and 1,3-dimethyl-3,4,5,6-tetrahydro-2(1H)-pyrimidinone (9.43 mL). The resulting bright yellow solution was allowed to stir at −78° C. for 1 h, at which time, a solution of iodomethylcyclopentane (7.95 g, 37.86 mmol) in 1,3-dimethyl-3,4,5,6-tetrahydro-2(1H)-pyrimidinone (7.08 mL) was slowly added. The reaction mixture was allowed to warm to 25° C. where it was stirred overnight. The reaction mixture was. then quenched with a saturated aqueous ammonium chloride solution (20 mL), and the layers were separated. The aqueous layer was extracted with ethyl acetate (3×20 mL). The combined organic layers were dried over sodium sulfate, filtered, and concentrated in vacuo. Flash chromatography (Merck Silica gel 60, 230–400 mesh, 95/5 hexanes/ethyl acetate) afforded 2-(3-chloro-4-methylsulfanyl-phenyl)-3-cyclopentyl-propionic acid methyl ester (5.74 g, 58.1%) as a colorless oil.

A solution of 2-(3-chloro-4-methylsulfanyl-phenyl)-3-cyclopentyl-propionic acid methyl ester (4.85 g, 15.50 mol) in ethanol (108 mL) was treated with a solution of potassium hydroxide (4.35 g, 77.50 mmol) in water (25.2 mL). The reaction mixture was stirred at 25° C. for 3 h. The reaction mixture was then concentrated in vacuo to remove ethanol. The resulting aqueous residue was acidified to pH=2 with a 1N aqueous hydrochloric acid solution and then extracted with methylene chloride (3×15 mL). The combined organic layers were then dried over sodium sulfate, filtered, and concentrated in vacuo to afford 2-(3-chloro-4-methylsulfanyl-phenyl)-3-cyclopentyl-propionic acid (4.14 g, 89.4%) as a white solid which was used without further purification.

A mixture of 2-(3-chloro-4-methylsulfanyl-phenyl)-3-cyclopentyl-propionic acid (4.14 g, 13.85 mmol) in formic acid (7.08 mL) was cooled to 0° C. and then treated with a 30% aqueous hydrogen peroxide solution (7.85 mL). Tetrahydrofuran (4 mL) was added to help solubilize the starting material. The resulting reaction mixture was allowed to warm to 25° C. where it was stirred at this temperature overnight. The reaction mixture was then cooled to 0° C. and slowly treated with a saturated aqueous sodium sulfite solution. The product was extracted into ethyl acetate (3×20 mL). The combined organic layers were dried over sodium sulfate, filtered, and concentrated in vacuo to afford 2-(3-chloro-4-methanesulfonyl-phenyl)-3-cyclopentyl-propionic acid (4.54 g, 99.1%) as a white solid: mp 123.9–126.2° C.; FAB-HRMS m/e calcd for $C_{15}H_{19}ClO_4S$ $(M+H)^+$ 331.0771, found 331.0776.

A solution of triphenylphosphine (238 mg, 0.91 mmol) in methylene chloride (6 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2-(3-chloro-4-methanesulfonyl-phenyl)-3-cyclopentyl-propionic acid (200 mg, 0.61 mmol). The resulting reaction mixture was stirred at 0° C. for 20 min and then allowed to warm to 25° C. where it was stirred for 30 min. The reaction mixture was then treated with 2-aminobenzoxazole (121 mg, 0.91 mmol) and pyridine (0.15 mL, 1.8 mmol) and was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded N-benzooxazol-2-yl-2-(3-chloro-4-methanesulfonyl-phenyl)-3-cyclopentyl-propionamide (166 mg, 61%) as a light pink foam: EI-HRMS m/e calcd for $C_{22}H_{23}ClN_2O_4S$ ($M^+$) 446.1067, found 446.1077.

EXAMPLE 17

N-Benzooxazol-2-yl-2(R)-(3-chloro-4-methanesulfonyl-phenyl)-3-cyclopentyl-propionamide

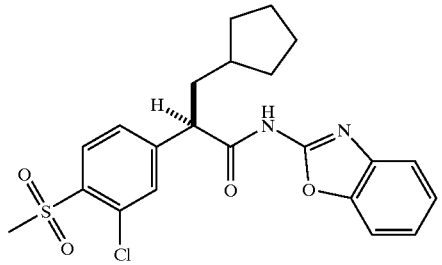

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (prepared as in Example 19, 200 mg, 0.61 mmol). The reaction mixture was stirred at 0° C. for 20 min and then allowed to warm to 25° C. where it was stirred for 30 min. The reaction mixture was then treated with 2-aminobenzoxazole (121 mg, 0.91 mmol) and pyridine (0.15 mL, 1.8 mmol), and the resulting reaction mixture was stirred at 25° C. for 16 h. The reaction was then diluted with water (15 mL) and extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded N-benzooxazol-2-yl-2(R)-(3-chloro-4-methanesulfonyl-phenyl)-3-cyclopentyl-propionamide (206 mg, 76%) as a light orange foam: $[\alpha]^{23}_{589}=-24.4°$ (c=0,119,chloroform); EI-HRMS m/e calcd for $C_{22}H_{23}ClN_2O_4S$ (M$^+$) 446.1067, found 446.1083.

EXAMPLE 18

N-Benzothiazol-2-yl-2-(3-chloro-4-methanesulfonyl-phenyl)-3-cyclopentyl-propionamide

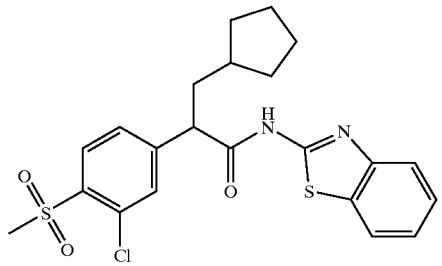

A solution of triphenylphosphine (238 mg, 0.91 mmol) in methylene chloride (6 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2-(3-chloro-4-methanesulfonyl-phenyl)-3-cyclopentyl-propionic acid (prepared as in Example 16, 200 mg, 0.61 mmol). The resulting reaction mixture was stirred at 0° C. for 20 min and then allowed to warm to 25° C. where it was stirred for 30 min. The reaction mixture was then treated with 2-aminobenzothiazole (136 mg, 0.91 mmol) and pyridine (0.15 mL, 1.8 mmol) and was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded N-benzothiazol-2-yl-2-(3-chloro-4-methanesulfonyl-phenyl)-3-cyclopentyl-propionamide (214 mg, 77%) as an off-white foam: EI-HRMS m/e calcd for $C_{22}H_{23}ClN_2O_3S_2$ (M$^+$) 462.0839, found 462.0833.

EXAMPLE 19

N-Benzothiazol-2-yl-2(R)-(3-chloro-4-methanesulfonyl-phenyl)-3-cyclopentyl-propionamide

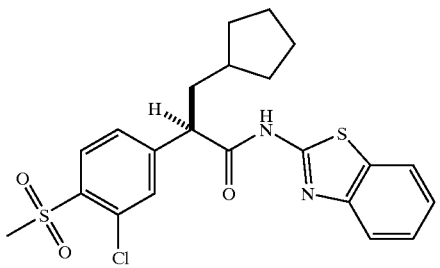

A mixture of 2-(3-chloro-4-methanesulfonyl-phenyl)-3-cyclopentyl-propionic acid (prepared as in Example 16, 6.07 g, 18.35 mmol), (R)-(+)-4-benzyl-2-oxazolidinone (2.83 g, 15.96 mmol), and triethylamine (6.68 mL, 47.71 mmol) in toluene (50 mL) was heated at 80° C. under argon until a homogeneous solution was obtained. The reaction mixture was then treated with trimethylacetyl chloride (3.55 mL, 28.81 mmol) in toluene (10 mL). The reaction mixture became yellow in color, and a precipitate formed. The reaction mixture was then heated at 80° C. for 36 h. The reaction mixture was allowed to cool to 25° C. and then concentrated in vacuo to remove toluene. The resulting residue was diluted with ethyl acetate (150 mL). The organic layer was washed with a 1N aqueous hydrochloric solution (1×100 mL), a 10% aqueous sodium carbonate solution (1×100 mL), and a saturated aqueous sodium chloride solution (1×100 mL). The organic layer was then dried over magnesium sulfate, filtered, and concentrated in vacuo. Flash chromatography (Merck Silica gel 60, 230–400 mesh, 90/5/5 methylene chloride/hexanes/ethyl acetate) afforded two products: (1) 4(R)-benzyl-3-[2(S)-(3-chloro-4-methanesulfonyl-phenyl)-3-cyclopentyl-propionyl]-oxazolidin-2-one (2.08 g, 23%) as a white foam: $[\alpha]^{23}_{589}=+10.4°$ (c=0.144, chloroform); FAB-HRMS m/e calcd for $C_{25}H_{28}ClNO_5S$ (M+H)$^+$ 490.1455, found 490.1457; and (2) 4(R)-benzyl-3-[2(R)-(3-chloro-4-methanesulfonyl-phenyl)-3-cyclopentyl-propionyl]-oxazolidin-2-one (2.20 g, 25%) as a white foam: $[\alpha]^{23}_{589}=-93.90°$(c=0.165, chloroform); FAB-HRMS m/e calcd for $C_{25}H_{28}ClNO_5S$ (M+H)$^+$ 490.1455, found 490.1443.

A solution of lithium hydroxide (215 mg, 9.0 mmol) in water (2.8 mL) was treated with a 30% aqueous hydrogen peroxide solution (2.0 mL, 18 mmol). This freshly prepared lithium hydroperoxide solution was then cooled to 0° C. and then slowly added to a cooled (0° C.) solution of the 4(R)-benzyl-3-[2(R)-(3-chloro-4-methanesulfonyl-phenyl)-3-cyclopentyl-propionyl]-oxazolidin-2-one (2.20 g, 4.5 mmol) in tetrahydrofuran (18 mL) and water (5.8 mL). After 1.5 h at 0° C, the reaction mixture was quenched with a 1.5N aqueous sodium sulfite solution (25 mL) and then diluted with water (150 mL). The aqueous layer was extracted with diethyl ether (3×50 mL). The aqueous layer was then acidified with a 1N aqueous hydrochloric acid solution to pH=2 and extracted with ethyl acetate (3×50 mL). The combined organic layers were dried over sodium sulfate, filtered, and concentrated in vacuo. Flash chromatography (Merck Silica gel 60, 230–400 mesh, 75/25 hexanes/ethyl acetate with 1% acetic acid) afforded 2(R)-(3-chloro-4-methanesulfonyl-phenyl)-3-cyclopentyl-propionic acid (1.26 g, 85%) as a white solid: mp 106.1–108.8° C.; $[\alpha]^{23}_{589}$=–43.0° (c=0.172, chloroform); EI-HRMS m/e calcd for $C_{15}H_{19}ClO_4S$ (M$^+$) 330.0692, found 330.0690.

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (200 mg, 0.61 mmol). The reaction mixture was stirred at 0° C. for 20 min and then allowed to warm to 25° C. where it was stirred for 30 min. The reaction mixture was then treated with 2-aminobenzothiazole (136 mg, 0.91 mmol) and pyridine (0.15 mL, 1.81 mmol), and the reaction mixture was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded N-benzothiazol-2-yl-2(R)-(3-chloro-4-methanesulfonyl-phenyl)-3-cyclopentyl-propionamide (205 mg, 73%) as a white foam: $[\alpha]^{23}_{589}$=–38.6° (c=0.044, chloroform); EI-HRMS m/e calcd for $C_{22}H_{23}ClN_2O_3S_2$ (M$^+$) 462.0839, found 462.0839.

EXAMPLE 20

N-(1H-Benzoimidazol-2-yl)-2-(3-chloro-4-methanesulfonyl-phenyl)-3-cyclopentyl-propionamide

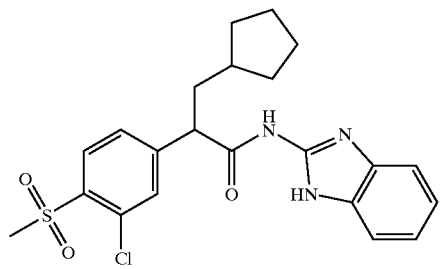

A solution of triphenylphosphine (118 mg, 0.45 mmol) in methylene chloride (5 mL) was cooled to 0° C. and then treated with N-bromosuccinimide (91 mg, 0.51 mmol). The reaction mixture was stirred at 0° C. until it became homogeneous. The resulting light purple reaction mixture was then treated with 2-(3-chloro-4-methanesulfonyl-phenyl)-3-cyclopentyl-propionic acid (prepared as in Example 16, 100 mg, 0.30 mmol). The reaction mixture was stirred at 0° C. for 20 min and then allowed to warm to 25° C. where it was stirred for 30 min. The reaction mixture was then treated with 2-aminobenzimidazole (60 mg, 0.45 mmol) and pyridine (0.073 mL, 0.91 mmol). The resulting reaction mixture was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded N-(1H-benzoimidazol-2-yl)-2-(3-chloro-4-methanesulfonyl-phenyl)-3-cyclopentyl-propionamide (44 mg, 33%) as a cream colored solid: EI-HRMS m/e calcd for $C_{22}H_{24}ClN_3O_3S$ (M+) 445.1227, found 445.1213.

EXAMPLE 21

N-(1H-Benzoimidazol-2-yl)-2(R)-(3-chloro-4-methanesulfonyl-phenyl)-3-cyclopentyl-propionamide

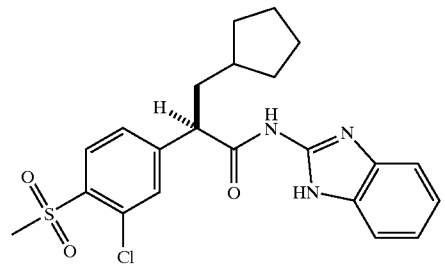

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (prepared as in Example 19, 200 mg, 0.61 mmol). The reaction mixture was stirred at 0° C. for 20 min and then allowed to warm to 25° C. where it was stirred for 30 min. The reaction mixture was then treated with 2-aminobenzimidazole (121 mg, 0.91 mmol) and pyridine (0.15 mL, 1.82 mmol), and the resulting reaction mixture was stirred at 25° C. for 16 h. The reaction mixture was then diluted with water (15 mL) and extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded the N-(1H-benzoimidazol-2-yl)-(R)-(3-chloro-4-methanesulfonyl-phenyl)-3-cyclopentyl-propionamide (150 mg, 56%) as a light brown solid: mp>215° C.; $[\alpha]^{23}_{589}$=–21.9° (c=0.041, chloroform); EI-HRMS m/e calcd for $C_{22}H_{24}ClN_3O_3S$ (M$^+$) 445,1227, found 445.1235.

EXAMPLE 22

2-(3-Chloro-4-methanesulfonyl-phenyl)-3-cyclopentyl-N-quinolin-2-yl-propionamide

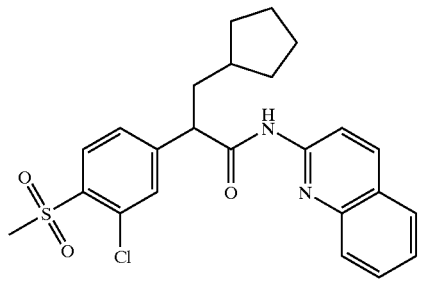

A solution of 2-(3-chloro-4-methanesulfonyl-phenyl)-3-cyclopentyl-propionic acid (prepared as in Example 16, 50 mg, 0.15 mmol) in methylene chloride (1 mL) was treated with N,N-dimethylformamide (1 drop) and then cooled to 0° C. The reaction mixture was then treated dropwise with a 2M solution of oxalyl chloride in methylene chloride (0.11 mL, 0.23 mmol) and stirred at 0° C. for 30 min. The reaction mixture was then treated with a solution of 2-aminoquinoline (33 mg, 0.23 mmol) and pyridine (0.06 mL, 0.755 mmol) in N,N-dimethylformamide (2.5 mL). The resulting reaction mixture was allowed to warm to 25° C. where it was stirred for 16 h. The reaction mixture was then diluted with water (10 mL) and extracted with ethyl acetate (3×15 mL). The combined organic layers were dried over sodium sulfate, filtered, and concentrated in vacuo. Biotage chromatography (FLASH 40S, Silica, 80/20 hexanes/ethyl acetate) afforded 2-(3-chloro-4-methanesulfonyl-phenyl)-3-cyclopentyl-N-quinolin-2-yl-propionamide (46 mg, 66%) as a light yellow oil: EI-HRMS m/e calcd for $C_{24}H_{25}ClN_2O_3S$ ($M^+$) 457.1346, found 457.1353.

EXAMPLE 23

2(R)-(3-Chloro-4-methanesulfonyl-phenyl)-3-cyclopentyl-N-quinolin-2-yl-propionamide

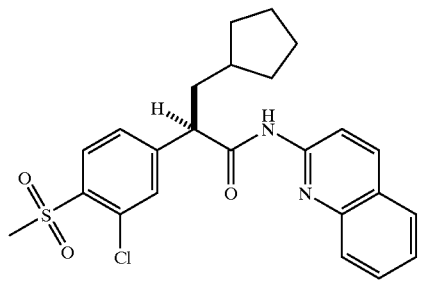

A solution of 2(R)-(3-chloro-4-methanesulfonyl-phenyl)-3-cyclopentyl-propionic acid (prepared as in Example 19, 200 mg, 0.61 mmol) in methylene chloride (4 mL) was treated with N,N-dimethylformamide (1 drop) and then cooled to 0° C. The reaction mixture was then treated dropwise with a 2M solution of oxalyl chloride in methylene chloride (0.45 mL, 0.91 mmol) and stirred at 0° C. for 30 min. The reaction mixture was then treated with a solution of 2-aminoquinoline (131 mg, 0.91 mmol) and pyridine (0.25 mL, 3.03 mmol) in N,N-dimethylformamide (10 mL). The resulting reaction mixture was allowed to warm to 25° C. where it was stirred for 16 h. The reaction mixture was then diluted with water (10 mL) and extracted with ethyl acetate (3×15 mL). The combined organic layers were dried over sodium sulfate, filtered, and concentrated in vacuo. Biotage chromatography (FLASH 40S, Silica, 70/30 hexanes/ethyl acetate) afforded 2(R)-(3-chloro-4-methanesulfonyl-phenyl)-3-cyclopentyl-N-quinolin-2-yl-propionamide (93 mg, 34%) as an off-white foam: EI-HRMS m/e calcd for $C_{24}H_{25}ClN_2O_3S$ ($M^+$) 456.1274, found 456.1268.

EXAMPLE 24

(A) N-(1H-Benzoimidazol-2-yl)-2-(3-bromo-4-methanesulfonyl-phenyl)-3-cyclopentyl-propionamide

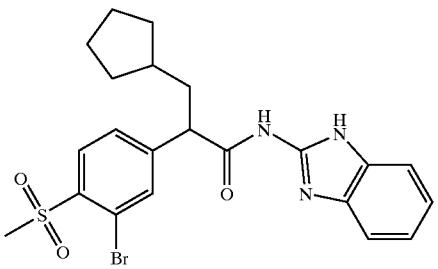

A solution of 4-(methylthio)phenylacetic acid (6.91 g, 37.9 mmol) in methanol (100 mL) was treated slowly with concentrated sulfuric acid (1 mL). The resulting reaction mixture was heated under reflux for 19 h. The reaction mixture was allowed to cool to 25° C. and then concentrated in vacuo to remove methanol. The resulting residue was diluted with ethyl acetate (200 mL). The organic layer was washed with a saturated aqueous sodium bicarbonate solution (3×300 mL) and a saturated aqueous sodium chloride solution (1×100 mL). The organic layer was dried over sodium sulfate, filtered, and concentrated in vacuo to afford (4-methylsulfanyl-phenyl)-acetic acid methyl ester (7.28 g, 98%) as a yellow liquid which was used without further purification: EI-HRMS m/e calcd for $C_{10}H_{12}O_2S$ ($M^+$) 196.0558, found 196.0559.

A solution of (4-methylsulfanyl-phenyl)-acetic acid methyl ester (7.28 g, 37.1 mmol) in carbon tetrachloride (150 mL) was slowly treated with bromine (2.5 mL, 48.23 mmol). The reaction mixture was stirred at 25° C. for 3 h, at which time, thin layer chromatography still indicated the presence of a substantial amount of starting material. The reaction mixture was treated with more bromine (2.5 mL, 48.23 mmol). The reaction mixture was stirred an additional 1 h at 25° C. and then quenched with a 10% aqueous sodium bisulfite solution (200 mL). The reaction mixture was concentrated in vacuo to remove carbon tetrachloride. The resulting aqueous layer was extracted with ethyl acetate (3×200 mL). The combined organic layers were dried over sodium sulfate, filtered and concentrated in vacuo. Flash chromatography (Merck Silica gel 60, 70–230 mesh, 9/1 hexanes/ethyl acetate) afforded (3-bromo-4-methylsulfanyl-phenyl)-acetic acid methyl ester (8.57 g, 84%) as a light yellow oil: EI-HRMS m/e calcd for $C_{10}H_{11}BrO_2S$ ($M^+$) 273.9663, found 273.9661.

A solution of diisopropylamine (4.8 mL, 34.27 mmol) in dry tetrahydrofuran (30 mL) and 1,3-dimethyl-3,4,5,6-tetrahydro-2(1H)-pyrimidinone (10 mL) was cooled to −78° C. under nitrogen and then treated with a 2.5M solution of n-butyllithium in hexanes (13.8 mL, 34.27 mmol). The resulting reaction mixture was stirred at −78° C. for 30 min and then treated dropwise with a solution of (3-bromo-4-methylsulfanyl-phenyl)-acetic acid methyl ester (8.57 g, 31.15 mmol) in dry tetrahydrofuran (30 mL) and 1,3-dimethyl-3,4,5,6-tetrahydro-2(1H)-pyrimidinone (10 mL). The resulting reaction mixture was allowed to stir at −78° C. for 1 h, at which time, a solution of iodomethylcyclopentane (7.85 g, 37.38 mmol) in a small amount of dry tetrahydrofuran was added dropwise. The reaction mixture was allowed to warm to 25° C. where it was stirred for 15 h. The reaction mixture was quenched with water (300 mL) and then concentrated in vacuo to remove tetrahydrofuran. The remaining aqueous phase was extracted with ethyl acetate (3×150 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded 2-(3-bromo-4-methylsulfanyl-phenyl)-3-cyclopentyl-propionic acid methyl ester (9.20 g, 83%) as a light yellow oil: EI-HRMS m/e calcd for $C_{16}H_{21}BrO_2S$ ($M^+$) 356.0446, found 356.0435.

A solution of 2-(3-bromo-4-methylsulfanyl-phenyl)-3-cyclopentyl-propionic acid methyl ester (9.20 g, 25.75 mmol) in formic acid (30 mL) was cooled to 0° C. and then treated with a 30% aqueous hydrogen peroxide solution (15.0 mL, 386.25 mmol). The resulting solution was allowed to warm to 25° C. where it was stirred for 1.5 h. An additional amount of 30% aqueous hydrogen peroxide solution (5.0 mL, 43.00 mmol) was then added and the reaction was stirred at 25° C. for 3 h. The reaction was then re-cooled to 0° C., quenched with a saturated aqueous sodium bisulfite solution, and then extracted with ethyl acetate (2×300 mL). The combined organic layers were washed with a saturated aqueous sodium bicarbonate solution (2×200 mL), dried over sodium sulfate, filtered, and concentrated in vacuo to afford 2-(3-bromo-4-methanesulfonyl-phenyl)-3-cyclopentyl-propionic acid methyl ester (10.02 g, 100%) as a colorless gum which was used without further purification. EI-HRMS m/e calcd for $C_{16}H_{19}BrO_4S$ ($M^+$) 388.0344, found 388.0343.

A solution of 2-(3-bromo-4-methanesulfonyl-phenyl)-3-cyclopentyl-propionic acid methyl ester (10.02 g, 25.75 mol) in methanol (100 mL) and water (100 mL) was treated with lithium hydroxide (15.4 g, 515 mmol). The reaction mixture was stirred at 25° C. for 2 h. The reaction mixture was then concentrated in vacuo to remove methanol. The resulting aqueous residue was acidified to pH=2 with a 10% aqueous hydrochloric acid solution and then extracted with ethyl acetate (1×400 mL). The organic layer was washed with water (1×300 mL) and a saturated aqueous sodium chloride solution (1×300 mL). The organic layer was then dried over sodium sulfate, filtered, and concentrated in vacuo to afford 2-(3-bromo-4-methanesulfonyl-phenyl)-3-cyclopentyl-propionic acid (9.58 g, 99%) as a white solid which was used without further purification: mp 149–150° C.; FAB-HRMS m/e calcd for $C_{15}H_{19}BrO_4S$ $(M+H)^+$ 375.0266, found 375.0274.

A solution of 2-(3-bromo-4-methanesulfonyl-phenyl)-3-cyclopentyl-propionic acid (100 mg, 0.266 mmol), triethylamine (110 μL, 0.80 mmol), benzotriazol-1-yloxy-tris(dimethylamino)phosphonium hexafluorophosphate (187 mg, 0.42 mmol), and 2-aminobenzimidazole (56 mg, 0.42 mmol) in methylene chloride (10 mL) was stirred at 25° C. for 1.5 h. The reaction mixture was partitioned between water and methylene chloride. The organic layer was washed sequentially with a 1N aqueous hydrochloric acid solution (1×mL), water (1×10 mL), and a saturated aqueous sodium bicarbonate solution (1×10 mL). The organic layer was then dried over magnesium sulfate, filtered, and concentrated in vacuo. Biotage chromatography (FLASH 40S, Silica, 19/1 chloroform/methanol) afforded N-(1H-benzoimidazol-2-yl)-2-(3-bromo-4-methanesulfonyl-phenyl)-3-cyclopentyl-propionamide (69 mg, 53%) as a white solid: mp>220° C.; EI-HRMS m/e calcd for $C_{22}H_{24}BrN_3O_3S$ ($M^+$) 489.0722, found 489.0727.

(B) In an Analogous Manner, There Were Obtained

From 2-(3-bromo-4-methanesulfonyl-phenyl)-3-cyclopentyl-propionic acid and 2-aminobenzothiazole: N-benzothiazol-2-yl-2-(3-bromo-4-methanesulfonyl-phenyl)-3-cyclopentyl-propionamide as a white solid: mp 165–168° C.; EI-HRMS m/e calcd for $C_{22}H_{23}BrN_2O_3S_2$ ($M^+$) 506.0333, found 506.0330.

From 2-(3-bromo-4-methanesulfonyl-phenyl)-3-cyclopentyl-propionic acid and 2-aminobenzoxazole: N-benzooxazol-2-yl-2-(3-bromo-4-methanesulfonyl-phenyl)-3-cyclopentyl-propionamide as an off-white solid: mp 102–105° C.; EI-HRMS m/e calcd for $C_{22}H_{23}BrN_2O_4S$ ($M^+$) 490.0562, found 490.0554.

EXAMPLE 25

2-(3-Bromo-4-methanesulfonyl-phenyl)-3-cyclopentyl-N-quinolin-2-yl-propionamide

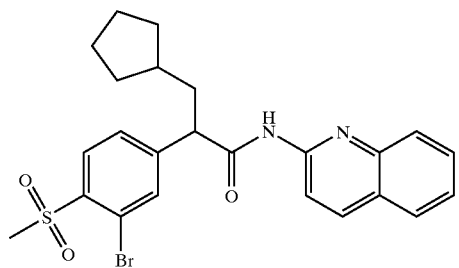

A solution of 2-(3-bromo-4-methanesulfonyl-phenyl)-3-cyclopentyl-propionic acid (prepared as in Example 24, 100 mg, 0.266 mmol) in methylene chloride (8 mL) was treated with dry N,N-dimethylformamide (2 drops). The reaction mixture was cooled to 0° C. and then treated dropwise with a 2M solution of oxalyl chloride in methylene chloride (0.15 mL, 0.29 mmol). The reaction mixture was stirred at 0° C. for 10 min and then stirred at 25° C. for 30 min. The reaction mixture was then treated with N,N-diisopropylethylamine (0.11 mL, 0.63 mmol) followed by a solution of 2-aminoquinoline (92 mg, 0.56 mmol) in dry tetrahydrofuran (3 mL). The resulting reaction mixture was stirred at 25° C. for 17 h. The reaction mixture was concentrated in vacuo. The resulting residue was adsorbed onto silica gel (Merck Silica gel 60, 230–400 mesh) and then purified via Biotage chromatography (FLASH 40S, Silica, 3/2 hexanes/ethyl acetate) to afford the 2-(3-bromo-4-methanesulfonyl-phenyl)-3-cyclopentyl-N-quinolin-2-yl-propionamide (122 mg, 92%) as a white foam; mp 95–100° C. EI-HRMS m/e calcd for $C_{24}H_{25}BrN_2O_3S$ ($M^+$) 500.0769, found 500.0775.

EXAMPLE 26

N-Benzothiazol-2-yl-2-(3-cyano-4-methanesulfonyl-phenyl)-3-cyclopentyl-propionamide

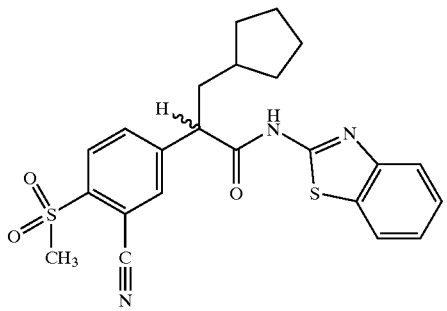

A solution of 4-(methylthio)phenylacetic acid (21.21 g, 116.38 mmol) in methanol (291 mL) was treated slowly with concentrated sulfuric acid (3 mL). The resulting reaction mixture was heated under reflux for 3 d. The reaction mixture was allowed to cool to 25° C. and then concentrated in vacuo to remove methanol. The resulting residue was diluted with diethyl ether (600 mL). The organic layer was washed with a saturated aqueous sodium bicarbonate solution (3×300 mL) and a saturated aqueous sodium chloride solution (1×300 mL). The organic layer was dried over sodium sulfate, filtered and concentrated in vacuo to afford (4-methylsulfanyl-phenyl)-acetic acid methyl ester (20.95 g, 92%) as a yellow liquid which was used without further purification: EI-HRMS m/e calcd for $C_{10}H_{12}O_2S$ ($M^+$) 196.0558, found 196.0559.

A solution of (4-methylsulfanyl-phenyl)-acetic acid methyl ester (5.11 g, 26.03 mmol) in carbon tetrachloride (130 mL) was treated slowly with bromine (1.74 mL, 33.84 mmol). The reaction mixture was stirred at 25° C. for 4 h, at which time, thin layer chromatography still indicated the presence of a substantial amount of starting material. The reaction mixture was further treated with more bromine (1.74 mL, 33.84 mmol). The reaction mixture was stirred an additional 4 h at 25° C. and then quenched with a 10% aqueous sodium bisulfite solution (150 mL). The reaction mixture was concentrated in vacuo to remove carbon tetrachloride. The resulting aqueous layer was extracted with ethyl acetate (3×150 mL). The combined organic layers were dried over sodium sulfate, filtered and concentrated in vacuo. Flash chromatography (Merck Silica gel 60, 70–230 mesh, 9/1 hexanes/ethyl acetate) afforded (3-bromo-4-methylsulfanyl-phenyl)-acetic acid methyl ester (6.10 g, 85%) as a light yellow oil: EI-HRMS m/e calcd for $C_{10}H_{11}BrO_2S$ ($M^+$) 273.9663, found 273.9661.

A solution of diisopropylamine (3.4 mL, 24.38 mmol) in dry tetrahydrofuran (21 mL) and 1,3-dimethyl-3,4,5,6-tetrahydro-2(1H)-pyrimidinone (7 mL) was cooled to −78° C. under nitrogen and then treated with a 2.5M solution of n-butyllithium in hexanes (9.8 mL, 24.38 mmol). The reaction mixture was stirred at −78° C. for 30 min and then treated dropwise with a solution of (3-bromo-4-methylsulfanyl-phenyl)-acetic acid methyl ester (6.10 g, 22.17 mmol) in dry tetrahydrofuran (21 mL) and 1,3-dimethyl-3,4,5,6-tetrahydro-2(1H)-pyrimidinone (7 mL).

The resulting reaction mixture was allowed to stir at −78° C. for 1 h, at which time, a solution of iodomethylcyclopentane (5.59 g, 26.60 mmol) in a small amount of dry tetrahydrofuran was added dropwise. The reaction mixture was allowed to warm to 25° C. where it was stirred for 15 h. The reaction mixture was quenched with water (300 mL) and then concentrated in vacuo to remove tetrahydrofuran. The remaining aqueous phase was extracted with ethyl acetate (3×150 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded 2-(3-bromo-4-methylsulfanyl-phenyl)-3-cyclopentyl-propionic acid methyl ester (4.52 g, 57%) as a light yellow oil: EI-HRMS m/e calcd for $C_{16}H_{21}BrO_2S$ ($M^+$) 356.0446, found 356.0435.

A solution of 2-(3-bromo-4-methylsulfanyl-phenyl)-3-cyclopentyl-propionic acid methyl ester (1.07 g, 2.99 mmol) in methylene chloride (15 mL) was treated with 3-chloroperoxybenzoic acid (57–86% grade, 1.81 g based on 57%, 5.99 mmol). The reaction mixture was stirred at 25° C. for 3 h. The reaction mixture was concentrated in vacuo to remove methylene chloride. The resulting residue was diluted with diethyl ether (300 mL). The organic phase was washed with a saturated aqueous sodium bicarbonate solution (3×200 mL) and a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 2-(3-bromo-4-methanesulfonyl-phenyl)-3-cyclopentyl-propionic acid methyl ester (1.09 g, 94%) as a colorless oil: ELI-HRMS m/e calcd for $C_6H_{19}BrO_4S$ ($M^+$) 388.0344, found 388.0343.

A mixture of 2-(3-bromo-4-methanesulfonyl-phenyl)-3-cyclopentyl-propionic acid methyl ester (990.0 mg, 2.54 mmol) and copper(I) cyanide (273.3 mg, 3.05 mmol) in dry N,N-dimethylformamide (2.5 mL) was heated under reflux for 4 h. The reaction was allowed to cool to 25° C., and the crude reaction mixture was directly purified without further chemical work-up. Flash chromatography (Merck Silica gel 60, 70–230 mesh, 100% hexanes then 3/1 hexanes/ethyl acetate) afforded 2-(3-cyano-4-methanesulfonyl-phenyl)-3-cyclopentyl-propionic acid methyl ester (646.5 mg, 76%) as a very light yellow oil: EI-HRMS m/e calcd for $C_{17}H_{21}NO_4S$ ($M^+$) 335.1191, found 335.1185.

A solution of 2-(3-cyano-4-methanesulfonyl-phenyl)-3-cyclopentyl-propionic acid methyl ester (4.84 g, 14.4 mol) in tetrahydrofuran (25 mL) was treated with a 0.8M aqueous lithium hydroxide solution (27 mL, 21.6 mmol). The reaction mixture was stirred at 25° C. for 2.5 h. The reaction mixture was partitioned between water and ethyl acetate and then acidified to pH=2 with a 10% aqueous hydrochloric acid solution. The layers were shaken and separated. The resulting organic layer was washed with a saturated aqueous sodium chloride solution, dried over magnesium sulfate, filtered, and concentrated in vacuo to afford crude 2-(3-cyano-4-methanesulfonyl-phenyl)-3-cyclopentyl-propionic acid (3.80 g, 82%) as a pale yellow oil that solidified to a pale yellow solid. An analytical sample was obtained by recrystallization from ethyl acetate to afford 2-(3-cyano-4- methanesulfonyl-phenyl)-3-cyclopentyl-propionic acid as a white solid: mp 180–181° C.; EI-HRMS m/e calcd for $C_{16}H_{19}NO_4S$ (M$^+$) 321.1034, found 321.1039.

A solution of 2-(3-cyano-4-methanesulfonyl-phenyl)-3-cyclopentyl-propionic acid (100 mg, 0.311 mmol), triethylamine (0.13 mL, 0.933 mmol), benzotriazol-1-yloxy-tris(dimethylamino)phosphonium hexafluorophosphate (206 mg, 0.467 mmol), and 2-aminobenzothiazole (70 mg, 0.467 mmol) in methylene chloride (3 mL) was stirred at 25° C. for 3 h. The crude reaction mixture was directly purified by Biotage chromatography (FLASH 40S, Silica, 1/1 hexanes/ethyl acetate) to afford N-benzothiazol-2-yl-2-(3-cyano-4-methanesulfonyl-phenyl)-3-cyclopentyl-propionamide (118 mg, 84%) as a white foam: mp 115-118° C. (foam to gel); EI-HRMS m/e calcd for $C_{23}H_{23}N_3O_3S_3$ (M$^+$) 453.1181, found 453.1173.

EXAMPLE 27

N-Benzooxazol-2-yl-2-(3-cyano-4-methanesulfonyl-phenyl)-3-cyclopentyl-propionamide

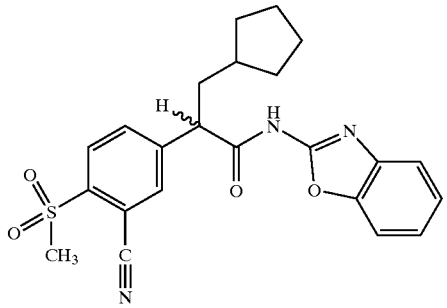

A solution of 2-(3-cyano-4-methanesulfonyl-phenyl)-3-cyclopentyl-propionic acid (prepared as in Example 26, 100 mg, 0.311 mmol), triethylamine (0.13 mL, 0.933 mmol), benzotriazol-1-yloxy-tris(dimethylamino)phosphonium hexafluorophosphate (206 mg, 0.467 mmol), and 2-aminobenzoxazole (63 mg, 0.467 mmol) in methylene chloride (3 mL) was stirred at 25° C. for 3 h. The reaction mixture was then diluted with water (40 mL), a 1N aqueous hydrochloric acid solution (5 mL), and ethyl acetate (40 mL). The layers were separated, and the organic layer was dried over magnesium sulfate, filtered, and concentrated in vacuo. Biotage chromatography (FLASH 40S, Silica, 1/1 hexanes/ethyl acetate) afforded N-benzooxazol-2-yl-2-(3-cyano-4-methanesulfonyl-phenyl)-3-cyclopentyl-propionamide (75 mg, 55%) as a yellow foam: mp 108–112° C.; EI-HRMS m/e calcd for $C_{23}H_{23}N_3O_4S$ (M$^+$) 437.1409, found 437.1409.

EXAMPLE 28

N-(1H-Benzoimidazol-2-yl)-2-(3-cyano-4-methanesulfonyl-phenyl)-3-cyclopentyl-propionamide

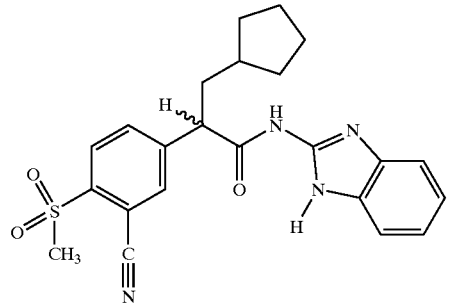

A solution of 2-(3-cyano-4-methanesulfonyl-phenyl)-3-cyclopentyl-propionic acid (prepared as in Example 26, 100 mg, 0.311 mmol), triethylamine (0.13 mL, 0.933 mmol), benzotriazol-1-yloxy-tris(dimethylamino)phosphonium hexafluorophosphate (206 mg, 0.467 mmol), and 2-aminobenzimidazole (62 mg, 0.467 mmol) in methylene chloride (3 mL) was stirred at 25° C. for 3 h. The crude reaction mixture was directly purified by Biotage chromatography (FLASH 40S, Silica, 1/3 hexanes/ethyl acetate) to afford N-(1H-benzoimidazol-2-yl)-2-(3-cyano-4-methanesulfonyl-phenyl)-3-cyclopentyl-propionamide (129 mg, 95%) as a yellow solid: mp 148–152° C.; EI-HRMS m/e calcd for $C_{23}H_{24}N_4O_3S$ (M$^+$)436.1569, found 436.1573.

EXAMPLE 29

2-(3-Cyano-4-methanesulfonyl-phenyl)-3-cyclopentyl-N-quinolin-2-yl-propionamide

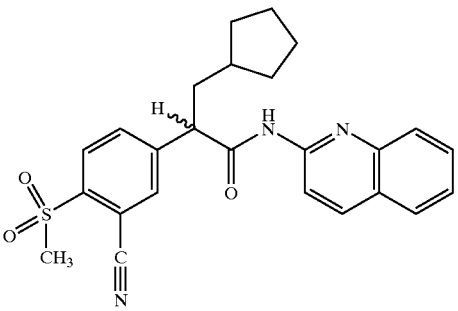

A solution of 2-(3-cyano-4-methanesulfonyl-phenyl)-3-cyclopentyl-propionic acid (prepared as in Example 26, 125 mg, 0.389 mmol) in methylene chloride (3 mL) was treated with N,N-dimethylformamide (1 drop) and then cooled to 0° C. The reaction mixture was then treated with oxalyl chloride (0.051 mL, 0.583 mmol). The resulting reaction mixture was allowed to warm to 25° C. where it was stirred for 1 h. The reaction mixture was then concentrated in vacuo. The resulting yellow gel was diluted with methylene chloride (2 mL) and then slowly added to a solution of 2-aminoquinoline (84 mg, 0.583 mmol) and triethylamine (0.108 mL, 0.778 mmol) in N, N-dimethylformamide (2 mL). The resulting reaction mixture was stirred at 25° C. for 20 h. The reaction mixture was then diluted with water (25 mL), a 1N aqueous hydrochloric acid solution (5 mL), and ethyl acetate (25 mL). The layers were separated, and the organic layer was dried over magnesium sulfate, filtered, and concentrated in vacuo. Biotage chromatography (FLASH 40S, Silica, 1/1 hexanes/ethyl acetate) afforded 2-(3-cyano-4-methanesulfonyl-phenyl)-3-cyclopentyl-N-quinolin-2-yl-propionamide (50.6 mg, 30%) as an off-white foam: mp 95–99° C. (foam to gel); EI-HRMS m/e calcd for $C_{25}H_{25}N_3O_3S$ ($M^+$) 447.1617, found 447.1616.

EXAMPLE 30

3-Cyclopentyl-2-(4-methanesulfonyl-3-trifluoromethyl-phenyl)-N-quinolin-2-yl-propionamide

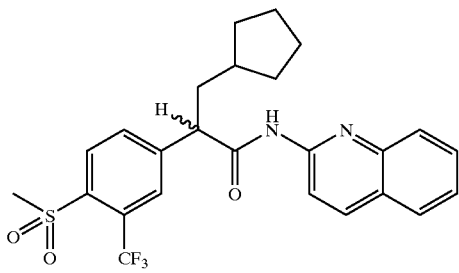

A solution of freshly prepared lithium diisopropylamide (35.3 mL of a 0.31M stock solution, 10.9 mmol) cooled to −78° C. was treated with (4-fluoro-3-trifluoromethyl-phenyl)-acetic acid (1.11 g, 5.0 mmol) in tetrahydrofuran/1,3-dimethyl-3,4,5,6-tetrahydro-2(1H)-pyrimidinone (3:1, 12.4 mL). The resulting solution was stirred at −78° C. for 1 h. At this time, the reaction was treated with a solution of iodomethylcyclopentane (1.16 g, 5.52 mmol) in 1,3-dimethyl-3,4,5,6-tetrahydro-2(1H)-pyrimidinone (1.2 mL). The reaction mixture was stirred at −78° C. for 4 h. The reaction was then warmed to 25° C. and was stirred at 25° C. for 48 h. This solution was then quenched by the slow addition of the reaction mixture to a 2N aqueous hydrochloric acid solution (50 mL). The product was extracted into ethyl acetate (3×100 mL) and diethyl ether (1×50 mL). The combined organic layers were dried over magnesium sulfate and sodium sulfate, filtered, and concentrated in vacuo. Flash chromatography (Merck Silica gel 60, 230–400 mesh, 50/50 hexanes/ethyl acetate with acetic acid) afforded 3-cyclopentyl-2-(4-fluoro-3-trifluoromethyl-phenyl)-propionic acid (1.28 g, 84.3%) as a white solid: mp 66–68° C.; EI-HRMS m/e calcd for $C_{15}H_{16}F_4O_2$ ($M^+$) 305.1165, found 305.1174.

A solution of 3-cyclopentyl-2-(4-fluoro-3-trifluoromethyl-phenyl)-propionic acid (7.77 g, 25.3 mmol) in methanol (50 mL) was treated slowly with concentrated sulfuric acid (0.01 mL). The resulting reaction mixture was heated under reflux for 24 h. The reaction mixture was allowed to cool to 25° C. and then concentrated in vacuo. The residue was dissolved in ethyl acetate (75 mL) and washed with a saturated aqueous sodium bicarbonate solution (1×50 mL), water (1×50 mL), and a saturated aqueous sodium chloride solution (4×50 mL). The combined organic layers were dried over magnesium sulfate and sodium sulfate, filtered, and concentrated in vacuo to afford 3-cyclopentyl-2-(4-fluoro-3-trifluoromethyl-phenyl)-propionic acid methyl ester (8.48 g, 87.5%) as yellow oil: EI-HRMS m/e calcd for $C_{16}H_{18}F_4O_2$ ($M^+$) 318.1243, found 318.1240.

A solution of 3-cyclopentyl-2-(4-fluoro-3-trifluoromethyl-phenyl)-propionic acid methyl ester (7.0 g, 21.9 mmol) in N,N-dimethylformamide (50 mL) was treated with sodium methanethiolate (2.61 g, 33.0 mmol). The reaction mixture was then heated at 100–110° C. for 24 h. At this time, the reaction was poured onto a mixture of ice and a 2N aqueous hydrochloric acid solution (100 mL). This mixture was extracted into ethyl acetate (3×75 mL) and diethyl ether (1×50 mL). The combined organic layers were then washed with water (1×75 mL) and a saturated aqueous sodium chloride solution (3×100 mL). The organic layer was dried over magnesium sulfate and sodium sulfate, filtered, and concentrated in vacuo. Flash chromatography (Merck Silica gel 60, 230–400 mesh, 85/15 hexanes/ethyl acetate) afforded 3-cyclopentyl-2-(4-methylsulfanyl-3-trifluoromethyl-phenyl)-propionic acid methyl ester (2.48g, 35.5%) as a pale yellow oil: EI-HRMS m/e calcd for $C_{17}H_{21}F_3O_2S$ ($M^+$) 346.1214, found 346.1212.

A solution of 3-cyclopentyl-2-(4-methylsulfanyl-3-trifluoromethyl-phenyl)-propionic acid methyl ester (2.36 g, 6.81 mmol) in methylene chloride (75 mL) at 25° C. was treated with 3-chloroperoxybenzoic acid (80–85% grade, 9.69 g, 40.1 mmol). The reaction mixture was stirred at 25° C. for 16 h. At this time, the reaction was diluted with methylene chloride (75 mL). The solution was sequentially washed with a saturated aqueous sodium bisulfite solution (2×50 mL), water (1×50 mL), a saturated aqueous sodium chloride solution (3×75 mL), a saturated aqueous sodium bicarbonate solution (1×75 mL), and a saturated aqueous sodium chloride solution (3×75 mL). The organic layer was dried over magnesium sulfate and sodium sulfate, filtered, and concentrated in vacuo to afford 3-cyclopentyl-2-(4-methanesulfonyl-3-trifluoromethyl-phenyl)-propionic acid methyl ester (2.88 g) as a clear oil: EI-HRMS m/e calcd for $C_{17}H_{21}F_3O_4S$ ($M^+$) 378.1112 found 3–78.1116.

A solution of 3-cyclopentyl-2-(4-methanesulfonyl-3-trifluoromethyl-phenyl)-propionic acid methyl ester (2.92 g, 7.72 mmol) in tetrahydrofuran/water (3:1, 88 mL) was treated with lithium hydroxide (647 mg, 15.43 mmol). The reaction was stirred at 25° C. for 3 d. The tetrahydrofuran was then removed in vacuo. The residue was diluted with water (50 mL) and extracted with diethyl ether (25 mL). The aqueous layer was acidified to pH=1 with a 3N aqueous hydrochloric acid solution. The product was extracted into ethyl acetate (3×75 mL) and diethyl ether (1×50 mL). The combined organic layers were washed with a saturated aqueous sodium chloride solution (2×100 mL), dried over magnesium sulfate and sodium sulfate, filtered, and concentrated in vacuo to give 3-cyclopentyl-2-(4-methanesulfonyl-3-trifluoromethyl-phenyl)-propionic acid (2.37 g, 84.5%) as a pale-yellow semi-solid: EI-HRMS m/e calcd for $C_{16}H_{19}F_3O_4S$ ($M^+$) 364.0956, found 364.0958.

A solution of 3-cyclopentyl-2-(4-methanesulfonyl-3-trifluoromethyl-phenyl)-propionic acid (182 mg, 0.5 mmol) in methylene chloride (5.0 mL) was cooled to 0° C. and then treated with a 2.0M solution of oxalyl chloride in methylene chloride (0.28 mL, 0.56 mmol) and a few drops of N,N- dimethylformamide. The reaction mixture was stirred at 0° C. for 15 min and at 25° C. for 30 min. The reaction mixture was then treated with a solution of 2-aminoquinoline (153 mg, 1.06 mmol) in tetrahydrofuran (2 mL) and triethylamine (0.17 mL, 1.20 mmol). This solution was stirred at 25° C. for 50 h. At this time, the reaction was concentrated in vacuo. Biotage chromatography (FLASH 40S, Silica 70/30 hexanes/ethyl acetate) afforded 3-cyclopentyl-2-(4-methanesulfonyl-3-trifluoromethyl-phenyl)-N-quinolin-2-yl-propionamide (140.3 mg, 57.2%) as a pale yellow solid: mp 90–95° C.; EI-HRMS m/e calcd for $C_{25}H_{25}F_3N_2O_3S$ (M$^+$) 490.1538, found 490.1532.

EXAMPLE 31

(A) N-Benzothiazol-2-yl-3-cyclopentyl-2-(4-methanesulfonyl-3-trifluoromethyl-phenyl)-propionamide

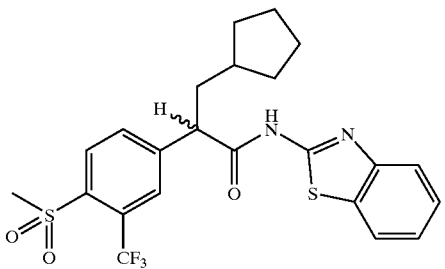

A solution of 3-cyclopentyl-2-(4-methanesulfonyl-3-trifluoromethyl-phenyl)-propionic acid (prepared as in Example 30, 182 mg, 0.50 mmol), benzotriazol-1-yloxy-tris(dimethylamino)phosphonium hexafluorophosphate (332 mg, 0.75 mmol), and 2-aminobenzothiazole (113 mg, 0.75 mmol) in methylene chloride (10 mL) at 25° C. was treated with triethylamine (0.21 mL, 1.50 mmol). The reaction mixture was stirred at 25° C. for 48 h. The reaction mixture was then diluted with methylene chloride (25 mL) and washed with a 3N aqueous hydrochloric acid solution (1×25 mL), water (1×25 mL), and a saturated aqueous sodium chloride solution (3×25 mL). The organic layer was dried over magnesium sulfate and sodium sulfate, filtered, and concentrated in vacuo. Biotage chromatography (FLASH 40S, Silica, 70/30 hexanes/ethyl acetate) afforded N-benzothiazol-2-yl-3-cyclopentyl-2-(4-methanesulfonyl-3-trifluoromethyl-phenyl)-propionamide (205 mg, 82.6%) as a white solid: mp 105–110° C.; EI-HRMS m/e calcd for $C_{23}H_{23}F_3N_2O_3S_2$ (M$^+$) 496.1102, found 496.1102.

(B) In an Analogous Manner, There Were Obtained

From 2-aminobenzimidazole and 3-cyclopentyl-2-(4-methanesulfonyl-3-trifluoromethyl-phenyl)-propionic acid: N-(1H-Benzoimidazol-2-yl)-3-cyclopentyl-2-(4-methanesulfonyl-3-trifluoromethyl-phenyl)-propionamide as a white solid: mp 168–171° C.; EI-HRMS m/e calcd for $C_{23}H_{24}F_3N_3O_3S$ (M$^+$) 479.1490, found 479.1489.

From 2-aminobenzoxazole and 3-cyclopentyl-2-(4-methanesulfonyl-3-trifluoromethyl-phenyl)-propionic acid: N-Benzooxazol-2-yl-3-cyclopentyl-2-(4-methanesulfonyl-3-trifluoromethyl-phenyl)-propionamide as an off-white solid: mp 100–105° C.; EI-HRMS m/e calcd for $C_{23}H_{23}F_3N_2O_4S$ (M$^+$) 480.1330, found 480.1329.

EXAMPLE 32

N-Benzothiazol-2-yl-3-cyclopentyl-2-(4-methanesulfonyl-3-nitro-phenyl)-propionamide

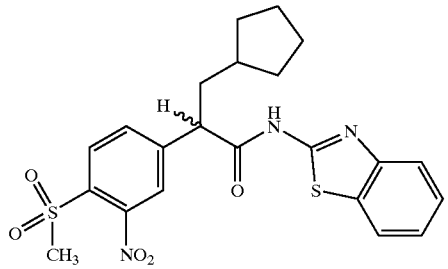

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitrophenylacetic acid methyl ester (1.91 g, 89%) as a yellow oil: EI-HRMS m/e calcd for $C_9H_8ClNO_4$ (M$^+$) 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) was cooled to −78° C. and then treated dropwise with a 2.5M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h, at which time, a solution of iodomethylcyclopentane (4.58 g, 21.8 mol) in a small amount of dry tetrahydrofuran was added dropwise. The reaction mixture was then stirred at −78° C. and then allowed to warm to 25° C. where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitrophenyl)-3-cyclopentyl-propionic acid methyl ester (2.17 g, 32%) as a yellow oil: EI-HRMS m/e calcd for $C_{15}H_{18}ClNO_4$ (M$^+$) 311.0924, found 311.0927.

A solution of 2-(4-chloro-3-nitrophenyl)-3-cyclopentyl-propionic acid methyl ester (1.00 g, 3.21 mmol) and sodium methanesulfinate (0.36 g, 3.53 mmol) in dimethyl sulfoxide (3 mL) was heated at 130° C. for 5 h. The black reaction mixture was then poured over ice (20 g), resulting in the formation of a brown sticky substance. The resulting mixture was then treated with ethyl acetate (50 mL) and water (50 mL), and the layers were separated. The aqueous layer was further extracted with ethyl acetate (2×50 mL). The combined organic layers were washed with a saturated aqueous sodium chloride solution, dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid methyl ester (0.95 g, 84%) as a yellow gel: FAB-HRMS m/e calcd for $C_{16}H_{21}NO_6S$ $(M+H)^+$ 356.1169, found 356.1175.

A solution of 3-cyclopentyl-2-(4-methanesulfonyl-3-nitrophenyl)-propionic acid methyl ester (1.17 g, 3.29 mmol) in tetrahydrofuran (6 mL) was treated with a 0.8M aqueous lithium hydroxide solution (6.17 mL, 4.94 mmol). The reaction mixture was stirred at 25° C. for 3 h. The reaction mixture was then diluted with water (50 mL), a 1N aqueous hydrochloric acid solution (10 mL), and ethyl acetate (50 mL). The layers were separated, and the aqueous layer was further extracted with ethyl acetate (2×50 mL). The combined organic layers were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid (993 mg, 88%) as a yellow foam which contained a small impurity. A small amount of the yellow foam (50 mg) was re-purified using Biotage chromatography (FLASH 40S, Silica, 3/1 then 1/1 hexanes/ethyl acetate) to afford 3-cyclopentyl-2-(4-methanesulfonyl-3-nitrophenyl)-propionic acid as a white foam: mp 114–118° C. (foam to gel); FAB-HRMS m/e calcd for $C_{15}H_{19}NO_6S$ $(M+H)^+$ 342.1011, found 342.1014.

A solution of 3-cyclopentyl-2-(4-methanesulfonyl-3-nitrophenyl)-propionic acid (50 mg, 0.15 mmol), triethylamine (0.060 mL, 0.44 mmol), benzotriazol-1-yloxy-tris(dimethylamino)phosphonium hexafluorophosphate (98 mg, 0.22 mmol), and 2-aminobenzothiazole (33 mg, 0.22 mmol) in N,N-dimethylformaniide (3 mL) was stirred at 25° C. for 3 h. The reaction mixture was then diluted with water (25 mL), a 1N aqueous hydrochloric acid solution (5 mL), and ethyl acetate (25 mL). The layers were separated. The resulting organic layer was washed with a saturated aqueous sodium chloride solution (1×25 mL), dried over magnesium sulfate, filtered, and concentrated in vacuo. Flash chromatography (Merck Silica gel 60, 230–400 mesh, 2/1 hexanes/ethyl acetate) afforded N-benzothiazol-2-yl-3-cyclopentyl-2-(4-methanesulfonyl-3-nitro-phenyl)-propionamide (31 mg, 45%) as a pale yellow foam: mp 108–113° C. (foam to gel); EI-HRMS m/e calcd for $C_{22}H_{23}N_3O_5S_2$ $(M^+)$ 473.1079, found 473.1077.

EXAMPLE 33

N-Benzooxazol-2-yl-3-cyclopentyl-2-(4-methanesulfonyl-3-nitro-phenyl)-propionamide

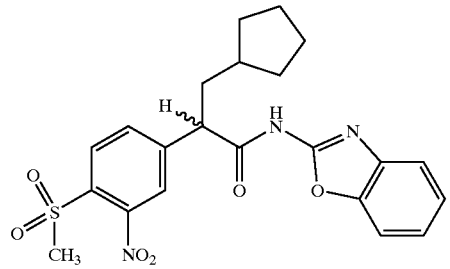

A solution of 3-cyclopentyl-2-(4-methanesulfonyl-3-nitrophenyl)-propionic acid (prepared as in Example 32, 50 mg, 0.15 mmol), triethylamine (0.060 mL, 0.44 mmol), benzotriazol-1-yloxy-tris(dimethylamino)phosphonium hexafluorophosphate (98 mg, 0.22 mmol), and 2-aminobenzoxazole (30 mg, 0.22 mmol) in N,N-dimethylformamide (3 mL) was stirred at 25° C. for 3 h. The reaction mixture was then diluted with water (25 mL), a 1N aqueous hydrochloric acid solution (5 mL), and ethyl acetate (25 mL). The layers were separated. The resulting organic layer was washed with a saturated aqueous sodium chloride solution (1×25 mL), dried over magnesium sulfate, filtered, and concentrated in vacuo. Flash chromatography (Merck Silica gel 60, 230–400 mesh, 2/1 hexanes/ethyl acetate) afforded N-benzooxazol-2-yl-3-cyclopentyl-2-(4-methanesulfonyl-3-nitro-phenyl)-propionamide (13 mg, 19.5%) as a yellow solid: mp 106–110° C; EI-HRMS m/e calcd for $C_{22}H_{23}N_3O_6S$ $(M^+)$ 457.1308, found 457.1323.

EXAMPLE 34

N-(1H-Benzoimidazol-2-yl)-3-cyclopentyl-2-(4-methanesulfonyl-3-nitro-phenyl)-propionamide

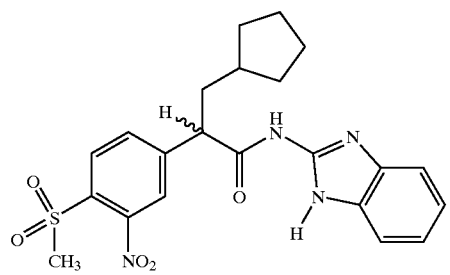

A solution of 3-cyclopentyl-2-(4-methanesulfonyl-3-nitrophenyl)-propionic acid (prepared as in Example 32, 50 mg, 0.15 mmol), triethylamine (0.060 mL, 0.44 mmol), benzotriazol-1-yloxy-tris(dimethylamino)phosphonium hexafluorophosphate (98 mg, 0.22 mmol), and 2-aminobenzimidazole (30 mg, 0.22 mmol) in N,N-dimethylformamide (3 mL) was stirred at 25° C. for 4 h. The reaction mixture was then diluted with water (25 mL), a 1N aqueous hydrochloric acid solution (5 mL), and ethyl acetate (25 mL). The layers were separated. The resulting organic layer was washed with a saturated aqueous sodium chloride solution (1×25 mL), dried over magnesium sulfate, filtered, and concentrated in vacuo. Biotage chromatography (FLASH 40S, Silica, 1/3 hexanes/ethyl acetate) afforded N-(1H-benzoimidazol-2-yl)-3-cyclopentyl-2-(4-methanesulfonyl-3-nitro-phenyl)-propionamide (25 mg, 38%) as a pale yellow solid: mp 113–117° C.; EI-HRMS m/e calcd for $C_{22}H_{24}N_4O_5S$ ($M^+$) 456.1467, found 456.1465.

EXAMPLE 35

3-Cyclopentyl-2-(4-methanesulfonyl-3-nitro-phenyl)-N-quinolin-2-yl-propionamide

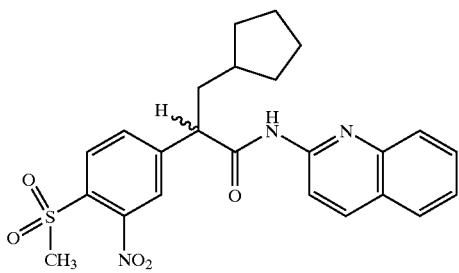

A solution of 3-cyclopentyl-2-(4-methanesulfonyl-3-nitrophenyl)-propionic acid (prepared as in Example 32, 150 mg, 0.439 mmol), triethylamine (0.184 mL, 1.32 mmol), benzotriazol-1-yloxy-tris(dimethylamino)phosphonium hexafluorophosphate (291 mg, 0.659 mmol), and 2-aminoquinoline (95 mg, 0.659 mmol) in methylene chloride (4 mL) was stirred at 25° C. overnight. The crude reaction mixture was directly purified by Biotage chromatography (FLASH 40M, Silica, 1/1 hexanes/ethyl acetate) to afford 3-cyclopentyl-2-(4-methanesulfonyl-3-nitro-phenyl)-N-quinolin-2-yl-propionamide (28 mg, 13.6%) as a white foam: mp 102–106° C. (foam to gel); EI-HRMS m/e calcd for $C_{24}H_{25}N_3O_5S$ ($M^+$) 467.1515, found 467.1513.

BIOLOGICAL ACTIVITY EXAMPLES

Example A: In Vitro Glucokinase Activity

Glucokinase Assay

Glucokinase (GK) was assayed by coupling the production of glucose-6-phosphate to the generation of NADH with glucose-6-phosphate dehydrogenase (G6PDH, 0.75–1 kunits/mg; Boehringer Manmheim, Indianapolis, Ind.) from *Leuconostoc mesenteroides* as the coupling enzyme (Scheme 2). Recombinant Scheme 2

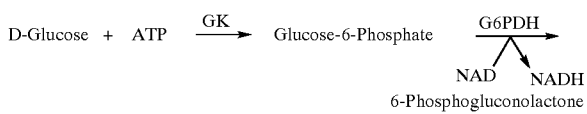

6-Phosphogluconolactone

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μL. The incubation mixture contained: 25 mM Hepes buffer (pH, 7.1), 25 mM KCl, 5 mM D-glucose, 1 mM ATP, 1.8 mM NAD, 2 mM $MgCl_2$ 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 μl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I and II described in the Synthesis Examples had an $SC_{1.5}$ less than or equal to 30 μM.

References for Example A

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J* 309: 167–173, 1995; and Neet, K., Keenan, R. P., and Tippett, P. S. Observation of a kinetic slow transition in monomeric glucokinase. Biochemistry 29;770–777, 1990.

Example B: In Vivo Activity

Glucokinase Activator in vivo Screen Protocol

C57BL/6J mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire44/14:PEG400q.s. 4:66:30 v/w/v. Mice are dosed orally with 7.5 μL formulation per gram of body weight to equal a 50 mg/kg dose. Immediately prior to dosing, a pre dose (time zero) blood glucose reading is acquired by snipping off a small portion of the animals tail (~1 mm) and collecting 15 μL blood into a heparinized capillary tube for analysis. Following GK activator administration, additional blood glucose readings are taken at 1, 2, 4, and 6 hours post dose from the same tail wound. Results are interpreted by comparing the mean blood glucose values of six vehicle treated mice with six GK activator treated mice over the six hour study duration. Compounds are considered active when they exhibit a statistically significant ($p \leq 0.05$) decrease in blood glucose compared to vehicle for two consecutive assay time points.

What is claimed is:

1. A compound of formula

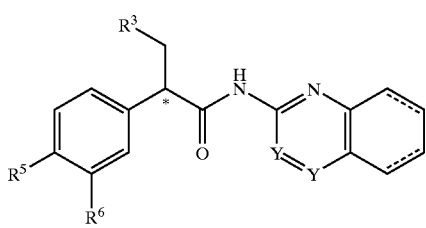

IIb or a pharmaceutically acceptable salt thereof; wherein
$R^3$ is a cycloalkyl having from 4 to 7 carbon atoms or 2-propyl;
$R^5$ is Cl or F;
$R^6$ is Cl or F;
each Y is independently CH or N;
dotted lines collectively represent 0 or 2 additional double bonds in the heterocyclic ring structure; and
* denotes an asymmetric carbon atom.

2. The compound of claim 1, wherein the amide is in the "R" configuration at the asymmetric carbon shown.

3. The compound of claim 1, wherein both $R^5$ and $R^6$ are Cl.

4. The compound of claim 3, wherein $R^3$ is cyclopentyl.

5. The compound of claim 4, wherein both Y are CH.

6. The compound of claim 5, wherein the amide is 3-cyclopentyl-2-(3,4-dichloro-phenyl)-N-quinolin-2-yl-propionamide.

7. The compound of claim 5, wherein the amide is 3-cyclopentyl-2(R)-(3,4-dichloro-phenyl)-N-quinolin-2-yl-propionamide.

8. The compound of claim 4, wherein at least one Y is N.

9. The compound of claim 1, wherein $R^3$ is cyclopentyl.

10. The compound of claim 1, wherein both Y are CH.

11. The compound of claim 9, wherein at least one Y is N.

12. The compound of claim 1, wherein both Y are CH.

13. The compound of claim 12, wherein the dotted lines represent 0 additional double bonds.

14. The compound of claim 12, wherein the dotted lines represent 2 additional double bonds.

15. The compound of claim 1, wherein at least one Y is N.

16. The compound of claim 15, wherein the dotted lines represent 0 additional double bonds.

17. The compound of claim 15, wherein the dotted lines represent 2 additional double bonds.

* * * * *